United States Patent
Chen et al.

(10) Patent No.: US 8,690,846 B2
(45) Date of Patent: Apr. 8, 2014

(54) COMBINATION OF TWO DISPOSABLE WASTE CONTAINMENT ARTICLES WORN SIMULTANEOUSLY

(75) Inventors: Ron Chen, Zichron Ya'akov (IL); Moshe D. Goldwasser, Tel Mond (IL); Stanley R. Kellenberger, Appleton, WI (US)

(73) Assignee: Tisteron, Ltd., Caesarea (IL)

( * ) Notice: Subject to any disclaimer, the term of this patent is extended or adjusted under 35 U.S.C. 154(b) by 400 days.

(21) Appl. No.: 13/065,288

(22) Filed: Mar. 17, 2011

(65) Prior Publication Data
US 2011/0213324 A1 Sep. 1, 2011

Related U.S. Application Data

(62) Division of application No. 11/901,635, filed on Sep. 17, 2007, now Pat. No. 7,927,320.

(60) Provisional application No. 60/845,771, filed on Sep. 20, 2006.

(51) Int. Cl.
*A61M 1/00* (2006.01)

(52) U.S. Cl.
USPC ............ 604/327; 604/317; 604/322; 4/144.1; 4/144.3

(58) Field of Classification Search
USPC ............ 604/317, 332, 337, 338, 344, 385.13; 4/144.1–144.3
See application file for complete search history.

(56) References Cited

U.S. PATENT DOCUMENTS

| | | |
|---|---|---|
| 4,252,120 A | 2/1981 | Carpenter |
| 4,309,782 A | 1/1982 | Paulin |
| 4,392,908 A | 7/1983 | Dehnel |

(Continued)

FOREIGN PATENT DOCUMENTS

| | | |
|---|---|---|
| CA | 2274649 | 6/1998 |
| EP | 0532002 | 3/1993 |

(Continued)

OTHER PUBLICATIONS

Stephen Brunauer, P.H. Emmet and Edward Teller, American Chemical Society, Adsorption of Gases in Multimolecular Layers, vol. 60, dated Feb. 1938, pp. 309-319 (11 pages), Published by American Chemical Society.

(Continued)

*Primary Examiner* — Melanie Hand
(74) *Attorney, Agent, or Firm* — Thomas J. Connelly; Wilhelm Law, S.C.

(57) ABSTRACT

A disposable waste containment article is disclosed along with a combination of using two articles simultaneously. The article includes a bodyside layer having a first surface and an outer perimeter, and a garment facing layer having an outer perimeter approximately coincident with the outer perimeter of the bodyside layer. An absorbent layer is positioned between the bodyside layer and the garment facing layer. A seal secures the bodyside layer to the garment facing layer. The seal is located inward of the outer perimeters. An ingress is formed in the bodyside layer and is aligned with one of the waste orifices present in a human body such that waste from the human body can pass through the ingress and be collected in the waste containment article. The waste containment article also includes a body adhesive for securing the first surface to the wearer's body.

22 Claims, 7 Drawing Sheets

(56) References Cited

U.S. PATENT DOCUMENTS

| | | |
|---|---|---|
| 4,445,898 A | 5/1984 | Jensen |
| 4,681,577 A | 7/1987 | Stern et al. |
| 4,784,656 A | 11/1988 | Christian |
| 4,917,692 A | 4/1990 | Steer et al. |
| 4,968,312 A | 11/1990 | Khan |
| D316,756 S | 5/1991 | Robbins |
| 5,028,224 A | 7/1991 | Pieper et al. |
| 5,102,585 A | 4/1992 | Pieper et al. |
| 5,147,343 A | 9/1992 | Kellenberger |
| 5,149,335 A | 9/1992 | Kellenberger et al. |
| 5,167,654 A | 12/1992 | Yang |
| 5,267,989 A | 12/1993 | Moyet-Ortiz |
| 5,306,269 A | 4/1994 | Lewis et al. |
| 5,364,382 A | 11/1994 | Latimer et al. |
| 5,384,174 A | 1/1995 | Ward et al. |
| 5,421,827 A | 6/1995 | Temple |
| 5,476,459 A | 12/1995 | Yang |
| 5,486,166 A | 1/1996 | Bishop et al. |
| 5,490,846 A | 2/1996 | Ellis et al. |
| 5,504,012 A | 4/1996 | Lipton |
| 5,520,669 A | 5/1996 | Mulholland |
| 5,522,810 A | 6/1996 | Allen, Jr. et al. |
| 5,562,646 A | 10/1996 | Goldman et al. |
| 5,562,650 A | 10/1996 | Everett et al. |
| 5,593,397 A | 1/1997 | La Gro |
| 5,599,335 A | 2/1997 | Goldman et al. |
| 5,669,894 A | 9/1997 | Goldman et al. |
| 5,695,484 A | 12/1997 | Cox |
| 5,709,747 A | 1/1998 | Goldwasser |
| 5,782,745 A | 7/1998 | Benderev |
| 5,865,926 A | 2/1999 | Wu et al. |
| 5,885,656 A | 3/1999 | Goldwasser |
| 5,941,860 A | 8/1999 | Wheeler |
| 5,941,864 A | 8/1999 | Roe et al. |
| 6,013,023 A | 1/2000 | Klingenstein |
| 6,096,057 A | 8/2000 | Klingenstein |
| 6,140,550 A | 10/2000 | Beihoffer et al. |
| 6,171,259 B1 | 1/2001 | Fisher |
| 6,183,847 B1 | 2/2001 | Goldwasser |
| 6,231,553 B1 | 5/2001 | Hulett |
| 6,297,335 B1 | 10/2001 | Funk et al. |
| 6,350,256 B1 | 2/2002 | Palumbo et al. |
| 6,398,768 B1 | 6/2002 | Palumbo et al. |
| 6,406,464 B1 | 6/2002 | Palumbo et al. |
| 6,464,674 B1 | 10/2002 | Palumbo et al. |
| 6,491,673 B1 | 12/2002 | Palumbo et al. |
| 6,508,794 B1 | 1/2003 | Palumbo et al. |
| 6,534,572 B1 | 3/2003 | Ahmed et al. |
| 6,551,292 B1 | 4/2003 | D'Acchioli et al. |
| 6,602,233 B1 | 8/2003 | Palumbo et al. |
| 6,607,516 B2 | 8/2003 | Cinelli et al. |
| 6,641,569 B1 | 11/2003 | Coles et al. |
| 6,646,179 B1 | 11/2003 | Melius et al. |
| 6,648,865 B1 | 11/2003 | Stiehl et al. |
| 6,652,502 B2 | 11/2003 | Bast et al. |
| 6,667,425 B1 | 12/2003 | Stiehl et al. |
| 6,669,677 B2 | 12/2003 | Burns et al. |
| 6,685,685 B2 | 2/2004 | Sugita et al. |
| 6,733,482 B1 | 5/2004 | Coles et al. |
| 6,790,798 B1 | 9/2004 | Suzuki et al. |
| 6,796,974 B2 | 9/2004 | Palumbo et al. |
| 6,833,488 B2 | 12/2004 | Bucevschi et al. |
| 6,840,924 B2 | 1/2005 | Buglino et al. |
| 6,843,766 B1 | 1/2005 | Nemir et al. |
| 6,878,756 B2 | 4/2005 | Cinelli et al. |
| 6,914,018 B1 | 7/2005 | Uitenbroek et al. |
| 6,916,312 B2 | 7/2005 | Kondo et al. |
| 6,921,574 B2 | 7/2005 | Cinelli et al. |
| 6,926,701 B2 | 8/2005 | Burns et al. |
| 6,939,914 B2 | 9/2005 | Qin et al. |
| 7,101,357 B2 | 9/2006 | Tanaka et al. |
| 2002/0072725 A1* | 6/2002 | Kolby-Falk ............... 604/385.01 |
| 2002/0103467 A1 | 8/2002 | Kubalak |
| 2002/0115971 A1 | 8/2002 | Holmes et al. |
| 2002/0169430 A1 | 11/2002 | Kirk et al. |
| 2003/0150050 A1* | 8/2003 | Tanaka et al. .................. 4/144.3 |
| 2004/0087923 A1 | 5/2004 | Cole |
| 2004/0167486 A1 | 8/2004 | Busam et al. |
| 2004/0253894 A1 | 12/2004 | Fell et al. |
| 2005/0015065 A1 | 1/2005 | Falconer |
| 2005/0143696 A1 | 6/2005 | Pedersen et al. |
| 2005/0222548 A1 | 10/2005 | Cinelli et al. |
| 2005/0261644 A1 | 11/2005 | Fields |
| 2007/0027435 A1 | 2/2007 | Nagakawa et al. |
| 2007/0078418 A1 | 4/2007 | May et al. |
| 2007/0142811 A1 | 6/2007 | Lais |
| 2007/0197984 A1 | 8/2007 | Richardson et al. |
| 2008/0065032 A1 | 3/2008 | Palmieri |
| 2009/0163885 A1 | 6/2009 | Pedersen et al. |

FOREIGN PATENT DOCUMENTS

| | | |
|---|---|---|
| EP | 0695541 | 2/1996 |
| WO | 9420547 | 9/1994 |
| WO | 00/00112 | 1/2000 |

OTHER PUBLICATIONS

Arthur W. Adamson, Physical Chemistry of Surfaces, Third Edition, Book, Copyright 1976, Title pages and Table of Contents (8 pages) enclosed, pp. 564-571 (4 pages) also enclosed, A Wiley-Interscience Publication by John Wiley & Sons, New York.

* cited by examiner

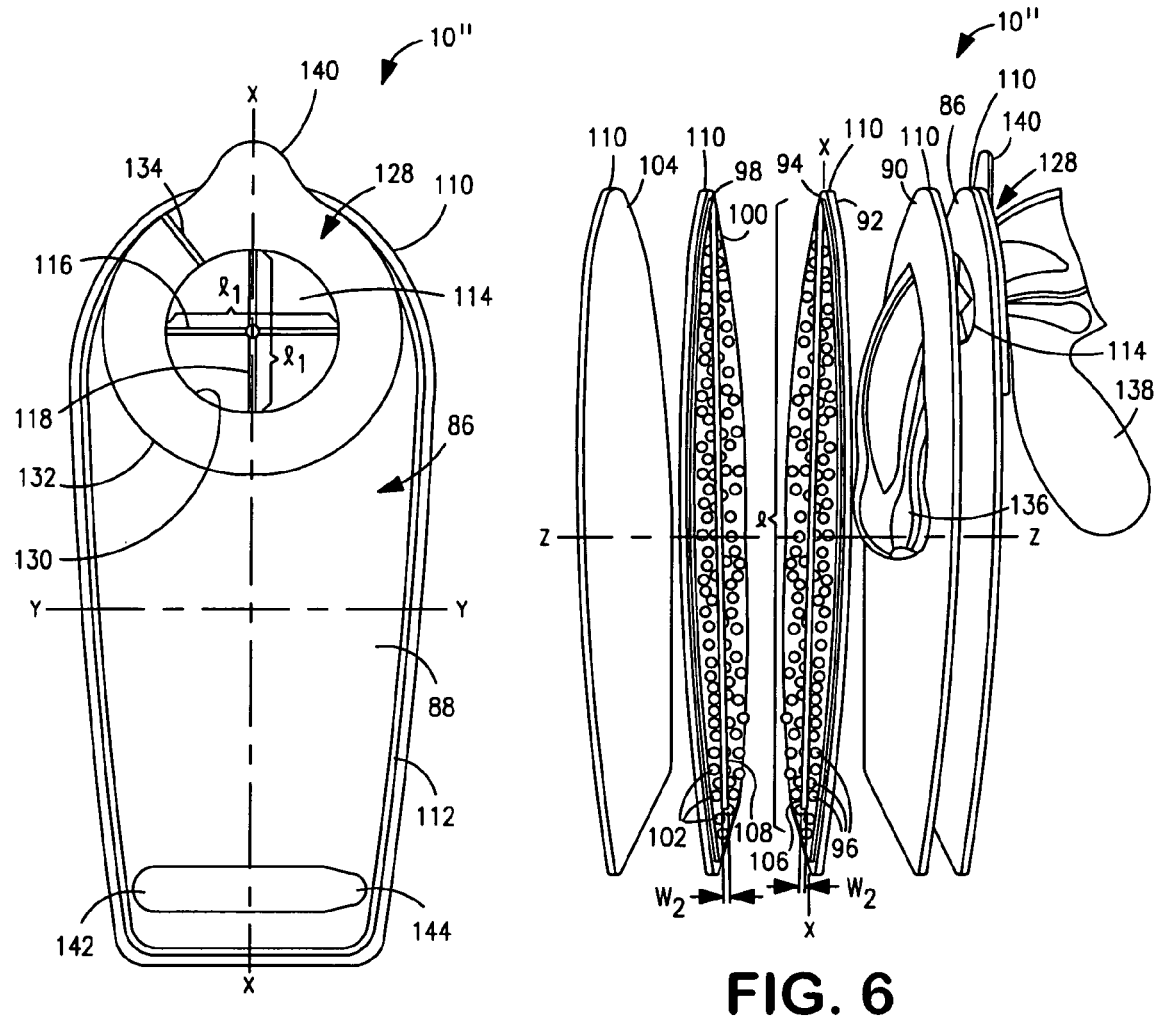
FIG. 5
FIG. 6
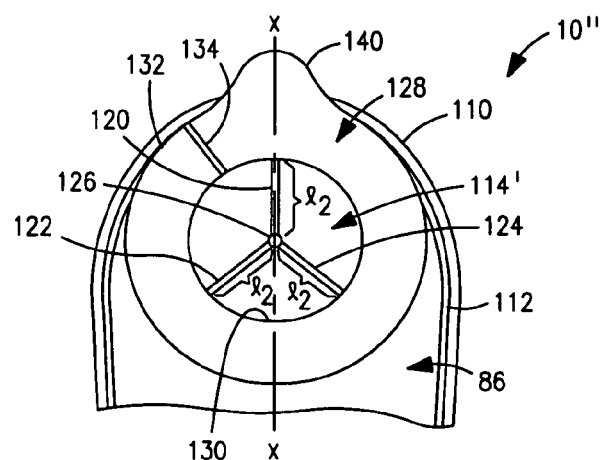
FIG. 7

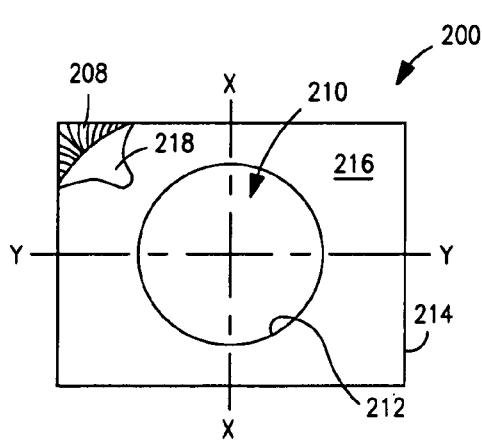
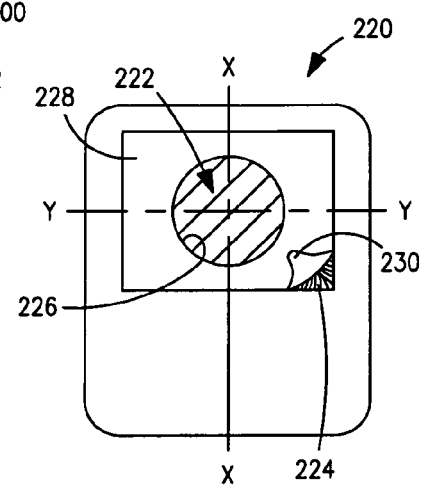
FIG. 12  FIG. 13  FIG. 14
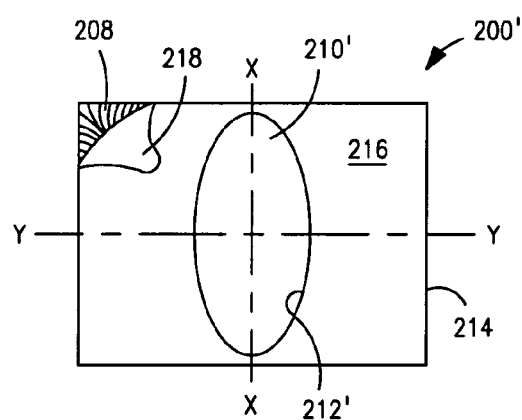
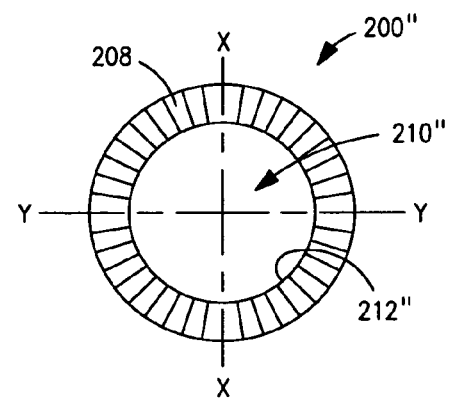
FIG. 15  FIG. 16
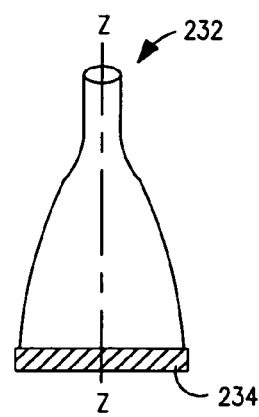
FIG. 17

COMBINATION OF TWO DISPOSABLE WASTE CONTAINMENT ARTICLES WORN SIMULTANEOUSLY

CROSS REFERENCE TO RELATED APPLICATIONS

This patent application claims priority under 35 U.S.C. §120, as a divisional application to U.S. patent application Ser. No. 11/901,635, filed Sep. 17, 2007, now U.S. Pat. No. 7,927,320, granted Apr. 19, 2001, which is a Non-Provisional Application of U.S. Provisional Patent Application Ser. No. 60/845,771, filed Sep. 20, 2006, which are incorporated herein by reference in their entireties.

FIELD OF THE INVENTION

This invention relates to a combination of two disposable waste containment articles which can be worn simultaneously by a person for the purpose of collecting body waste from two different orifices present in the human body.

BACKGROUND OF THE INVENTION

It has been known for many years to use disposable absorbent articles for collecting and disposing of human waste. Various sizes of such articles are available to collect waste from babies and small children, as a domestic use typically, and from adults, both as a domestic and institutional use. Such known disposable absorbent articles can be equipped with fasteners to secure the diaper to the wearer or have a unitary design where the disposable garment, such as training pants, is ready to wear. Other disposable absorbent articles, such as absorbent pads, are designed to be kept in place by reusable or disposable pants or undergarments.

In these known configurations, some disposable absorbent articles are designed to cope with both urine and feces. These disposable absorbent articles contain a unitary design which covers the entire crotch area of the wearer, spanning the urogenital and perianal areas.

Disposable absorbent diapers have specially designed features to cope with fecal material, both inside the diaper or by connection to an outside receptacle. However, in such instances, the disposable absorbent diapers are destined to be used as a single implement to collect and dispose of both urine and fecal material and thus are destined to cover the entire crotch area of the wearer.

The use of the above-identified disposable absorbent devices has proven to create issues relating to skin irritation, due to the close contact to the skin of a relatively large piece of absorbent material, and by the fact that the urine and/or feces discharged by the wearer are likely to be kept in contact with the skin of the wearer by the closely fitted absorbent article.

The use of disposable fecal management devices capable of collecting and retaining only fecal matter and disposable urine management devices capable of collecting and retaining only urine are known. However, such devices leave a lot to be desired relative to their ability to adequately collect waste material and keep it spaced apart from the wearer's skin.

Now, a disposable waste containment article has been invented which is capable of collecting body waste from one of the waste orifices present in a human body. This disposable waste containment article is more comfortable to wear, simple in construction and economical to manufacture. This disposable waste containment article is also more environmentally friendly than known diapers or training pants and is better suited for nursing and geriatric institution type facilities than heretofore known articles. Furthermore, these disposable waste containment articles are compact such that two articles can be worn simultaneously, one covering the urogenital area and a second covering the perianal area.

SUMMARY OF THE INVENTION

Briefly, this invention relates to a disposable waste containment article which is capable of collecting body waste from one of the waste orifices present in a human body and a combination of two articles worn simultaneously. The article includes a bodyside layer having a first surface and an outer perimeter and a garment facing layer having an outer perimeter approximately coincident with the outer perimeter of the bodyside layer. An absorbent layer is positioned between the bodyside layer and the garment facing layer. A seal bonds at least a portion of the bodyside layer to the garment facing layer. The seal is located inward of the outer perimeters. A body adhesive is secured to at least a portion of the first surface. An ingress is formed in the bodyside layer. The ingress is aligned with one of the waste orifices such that body waste from the human body can pass through the ingress and be collected in the waste containment article. One article can be aligned with a urethral orifice present in a human body and a second article can be aligned with an anal orifice present in the human body. In further embodiments, odor absorbing material is also included between the bodyside layer and the garment facing layer.

In another embodiment, a disposable waste containment article capable of collecting body waste from one of the waste orifices present in a human body includes a bodyside layer having a first surface and an outer perimeter and a garment facing layer having an outer perimeter approximately coincident with the outer perimeter of the bodyside layer. An absorbent layer is positioned between the bodyside layer and the garment facing layer. The absorbent layer has a major surface which contains superabsorbent. A seal bonds at least a portion of the bodyside layer to the garment facing layer. The seal is located inward of the outer perimeters. A gasket having an inner surface, an outer surface, an inner periphery and an outer periphery, is secured by its first surface to the first surface of the bodyside layer. The outer surface of the gasket has a body adhesive thereon and the inner periphery of the gasket is sized and configured to surround one of the waste orifices present in the human body. The disposable waste containment article further includes an enlarged aperture formed in the bodyside layer. The enlarged aperture is aligned with one of the waste orifices present in the human body such that body waste from the human body can pass through the enlarged aperture and be collected in the disposable waste containment article. One article can be aligned with a urethral orifice present in a human body and a second article can be aligned with an anal orifice present in the human body. In further embodiments, odor absorbing material is also included between the bodyside layer and the garment facing layer.

In still another embodiment, a disposable waste containment article capable of collecting body waste from one of the waste orifices present in a human body includes an anatomically shaped sticker having an enlarged aperture formed completely therethrough. The sticker has an outer periphery, an inner periphery, a first surface and an oppositely aligned second surface. A first adhesive is secured to the first surface of the sticker. The first adhesive allows the sticker to be removably attached to a human body such that the inner periphery surrounds one of the waste orifices. The disposable waste containment article also includes a closed, disposable collection receptacle having an opening formed therein. The opening is surrounded by a gasket with an enlarged aperture formed therethrough. The enlarged aperture has an inner periphery sized and configured to correspond with the inner periphery of the sticker. The gasket has a first surface and the collection receptacle contains a fluid absorbing material, and in a further embodiment, an odor absorbing material. A second adhesive is secured to the first surface of the gasket. The second adhesive allows the multiple collection receptacles to be repeatedly attached to and be removed from the second surface of the sticker.

A method of collecting body waste from one of the waste orifices present in a human body is also taught. The method includes the steps of removably attaching an anatomically shaped sticker to one of the waste orifices. The sticker has an enlarged aperture formed completely therethrough and has an outer periphery and an inner periphery. The sticker also has a first surface with a first adhesive secured thereto and an oppositely aligned second surface. The inner periphery of the sticker surrounds one of the waste orifices. A closed, disposable collection receptacle is removably secured to the second surface of the sticker. The disposable collection receptacle has an opening formed therein. The opening is surrounded by a gasket with an enlarged aperture formed therethrough. The enlarged aperture has an inner periphery sized and configured to correspond with the inner periphery of the sticker. The gasket has a first surface with a second adhesive secured thereto and the collection receptacle contains a fluid absorbing material, and in a further embodiment, an odor absorbing material.

The general object of this invention is to provide a disposable waste containment article and a combination of two articles worn simultaneously. A more specific object of this invention is to provide a disposable waste containment article that can be applied about an orifice located in the urogenital or perianal areas of a human body and a combination of two articles worn simultaneously.

Another object of this invention is to provide a disposable waste containment article capable of being worn by a male or a female.

A further object of this invention is to provide a disposable waste containment article capable of receiving and containing fluid waste, semi-solid waste and solid waste.

Still another object of this invention is to provide a disposable waste containment article that is capable of preventing urine and feces from contacting one another thus preventing urease from fecal material from converting urea in the urine into ammonia and thereby maintaining a relatively low urine pH level.

Still further, an object of this invention is to provide one or more disposable waste containment articles which can be utilized while the user is wearing a stretchable, elastic undergarment or some other type of confining undergarment.

Still another object of this invention is to provide a combination of two separate and distinct disposable waste containment articles that are worn simultaneously by a human being, one to collect urine and the other to collect fecal matter.

Other objects and advantages of the present invention will become more apparent to those skilled in the art in view of the following description and the accompanying drawings.

BRIEF DESCRIPTION OF THE DRAWINGS

FIG. 5 is a yet another embodiment of a disposable waste containment article designed to receive urine from a male.

FIG. 6 is an exploded perspective view of the disposable waste containment article shown in FIG. 5 and depicting five separate layers.

FIG. 7 is an enlarged view of the ingress formed in the bodyside layer which includes three slits emanating from a point.

FIG. 12 is a plan view of a sticker and a removable release layer, the sticker is designed to be directly attached to a wearer's skin after the release layer is removed and is sized to surround a waste orifice.

FIG. 13 is an end view of the sticker and release layer shown in FIG. 12.

FIG. 14 is a plan view of a fecal matter collection receptacle which can be removably attached to the sticker shown in FIG. 12.

FIG. 15 is a plan view of a sticker and a removable release layer, the sticker has an elongated shaped ingress designed to be directly attached to the skin of a female and sized to surround the urogenital area.

FIG. 16 is a plan view of a sticker having a circular opening formed therethrough which is designed to be directly attached to the skin of a male and sized to surround his penis.

FIG. 17 is a plan view of a urine collection receptacle which can be removably attached to the sticker shown in FIG. 16.

DETAILED DESCRIPTION OF THE INVENTION

Figure 1:
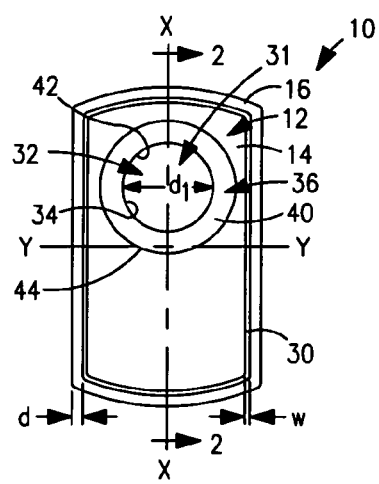
FIG. 1 is a front view of a disposable waste containment article depicting a body adhesive, a seal formed inward of the outer periphery of the bodyside layer and an ingress formed through the bodyside layer through which body waste can pass from a waste orifice present in a human body.
Figure 2:
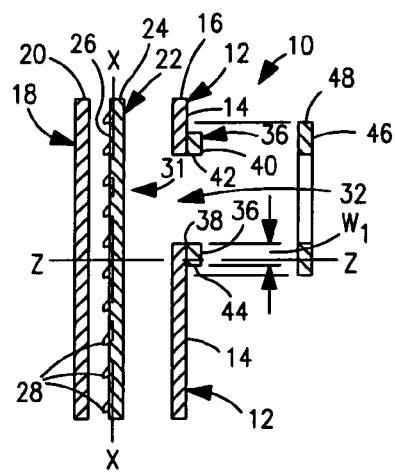
FIG. 2 is an exploded side view of the disposable waste containment article shown in FIG. 1 taken along line 2-2 without the seal which bonds two or more of the layers together, and with a removable release layer which overlies the adhesive to prevent it from becoming contaminated prior to being attached to the skin of a human body.

Referring to FIGS. 1 and 2, a disposable waste containment article 10 is shown which is capable of collecting body waste from one of the waste orifices present in a human body. The disposable waste containment article 10 has a longitudinal central axis X-X, a transverse central axis Y-Y, see FIG. 1, and a vertical central axis Z-Z, see FIG. 2. The waste orifices include the urethra, the vagina and the anus in a female, and the urethra (positioned within a male penis) and the anus in a male. By "disposable" it is meant an article which is designed and manufactured to be used only once and is then to be discarded after a single use. Such a disposable waste containment article 10 can be recycled, composted or otherwise disposed of in an environmentally compatible manner. The disposable waste containment article 10 is not intended to be laundered, restored or otherwise reused. By "body waste" it is meant urine, blood, menstrual fluid, menses, liquid feces, semi-solid fecal matter and solid fecal matter. Urine and excrement expelled after digestion, through either the urethra and/or the anus, can be conveniently captured by one or two of the disposable waste containment articles 10. The "anus" refers to the opening at the lower end of the alimentary canal through which semi-solid and solid waste is eliminated from a human body.

The disposable waste containment article 10 includes a bodyside layer 12 having a first surface 14 and an outer perimeter 16. The bodyside layer 12 faces the body or skin of the wearer of the disposable waste containment article 10. The bodyside layer 12 is liquid-impermeable so as to prevent a fluid from passing therethrough. The bodyside layer 12 can be formed from a liquid-impermeable material, such as a thermoplastic film or be treated or coated to acquire the characteristic of being liquid-impermeable. A polyolefin film, constructed or formed of polyethylene, polypropylene or a combination thereof, is a good liquid-impermeable material that can be utilized as the bodyside layer 12. The bodyside layer 12 can also be formed as a composite material having at least one layer that has liquid-impermeable qualities. It is also advantageous to make the bodyside layer 12 breathable, such that air and vapors can pass therethrough. Furthermore, the bodyside layer 12 should be constructed from a material that has a cloth-like feel, one that is soft to the touch. Desirably, the bodyside layer 12 is also formed from a material that is quiet and does not emit a noticeable noise or sound as it is compressed, folded, wrinkled, etc.

The bodyside layer 12 can be formed from a variety of materials known to those skilled in the art. For example, the bodyside layer 12 can utilize the cloth-like outer cover used in HUGGIES disposable diapers which are being commercially sold in Israel. HUGGIES is a registered trademark of Kimberly-Clark Corporation having an office in Neenah, Wis. 54956. The bodyside layer 12 can also be formed from microporous cloth-like laminates, such as are taught in U.S. Pat. No. 5,865,926. As mentioned above, the bodyside layer 12 can also be formed from suitable thermoplastic film materials, including but not limited to: polyolefins, especially polyethylene and polypropylene, amorphous polyolefins, and the like. The bodyside layer 12 can further be formed from material containing meltable components, such as fibers and/or polymeric binders. The fibers can be formed from natural fibers, such as cellulose-wood pulp, cotton, jute or hemp. Alternatively, the fibers can be formed from synthetic fibers, such as fiberglass, rayon, polyester, polyolefin, acrylic, polyamid, aramid, polytetrafluroethylene metal or polyimide. A combination of natural and synthetic fibers can also be used.

When a binder is present, it can be formed from various materials, including but not limited to: bicomponent high melt/low melt polymer, copolymer polyester, polyvinyl chloride, polyvinyl acetate/chloride copolymer, copolymer polyamide, materials including blends wherein some of the constituent materials are not meltable. The bodyside layer 12 can further be constructed from air and/or vapor permeable materials, including but not limited to: microporous films, such as those supplied by EXXON Chemical Co. III, U.S. under the designation EXXAIRE or those supplied by Mitsui Chemical Co., Japan under the designation ESPOIR. The bodyside layer 12 can further be formed from monolithic breathable materials, such as HYTREL available from DuPont or PEBAX available from ELF Atochem, France. Desirably, the bodyside layer 12 is constructed from a film, which may have more than one layer and which is permeable to gases, such as air and vapor, for example water vapor, in order to avoid the problem of entrapment and condensation of moisture vapor given off by the body of the wearer. By making the bodyside layer 12 permeable to gases, one can avoid the hot, clammy and uncomfortable conditions that can occur after a short period of using the disposable waste containment article 10. Although the above-identified breathable materials are best suited for use in forming the bodyside layer 12, non-breathable materials, for example materials impervious to air and/or moisture vapor can also be used. It has been found that non-breathable materials can best be used in those applications where the genitalia does not protrude into the disposable waste containment article 10. Lastly, the bodyside layer 12 can be formed from materials exhibiting extendable, expandable or stretchable qualities such as are taught in U.S. Pat. No. 6,914,018 and/or foldable qualities, such as taught in U.S. Pat. No. 6,685,685. These and other materials known to those skilled in the art can be used to construct the bodyside layer 12.

The bodyside layer 12 can also be formed from materials that are biodegradable, biocompatible and/or compostable. By "biodegradable" it is meant a material that is capable of being decomposed by biological agents, especially bacteria. By "biocompatible" it is meant a material that is biologically compatible by not producing a toxic, injurious or immunological response in living tissue. By "compostable" it is meant a material that can be converted to compost.

Referring to FIG. 2, the disposable waste containment article 10 also includes a garment facing layer 18. The garment facing layer 18 faces away from the wearer's body and towards an undergarment or outer clothing of the wearer. The garment facing layer 18 has an outer perimeter 20. The outer perimeter 20 is approximately coincident with the outer perimeter 16 of the bodyside layer 12. By "approximately coincident" it is meant within a distance of about 25 millimeters (mm). The garment facing layer 18 is also liquid-impermeable so as to prevent a fluid from passing therethrough. Like the bodyside layer 12, the garment facing layer 18 can be formed from a liquid-impermeable material, such as a thermoplastic film or be treated or coated to acquire the characteristic of being liquid-impermeable. A polyolefin film, constructed or formed of polyethylene, polypropylene or a combination thereof, is a good liquid-impermeable material that can be utilized as the garment facing layer 18. The garment facing layer 18 can also be formed as a composite material having at least one layer that has liquid-impermeable qualities. It is also advantageous to make the garment facing layer 18 breathable, such that air and vapors can pass therethrough. Furthermore, the garment facing layer 18 should be constructed from a material that has a cloth-like feel, one that is soft to the touch. Desirably, the garment facing layer 18 is also formed from a material that is quiet and does not emit a noticeable noise or sound as it is compressed, folded, wrinkled, etc. The garment facing layer 18 can be constructed from the same material used to make the bodyside layer 12, and described above, or it can be formed from a different material. The garment facing layer 18 can also be formed from materials that are biodegradable, biocompatible and/or compostable.

It should also be noted that the bodyside layer 12 and the garment facing layer 18 can be the same achromatic color, be of a color in the spectrum between white and black, or be formed of different colors. By "achromatic" it is meant a color having zero saturation or hue, such as white or black. Either the bodyside layer 12 and/or the garment facing layer 18 can be tinted, dyed, coated, painted, etc. or be formed from color filaments, fibers and/or binders so as to exhibit one or more pre-selected colors.

The disposable waste containment article 10 further includes an absorbent layer 22 positioned between the bodyside layer 12 and the garment facing layer 18. The absorbent layer 22 can be formed from a woven or a non-woven fabric. Desirably, the fabric is a non-woven material. By "woven" it is meant fabrics made by interlocking fibers by means such as weaving, knitting, or the like. By "non-woven" it is meant a fabric made of one or more natural fibers and/or synthetic fibers which are held together by means other than weaving. The non-woven typically does not include woven fibers, knitted fibers, or the like. By "fabric" it is meant a structural material.

Suitable examples of processes that can be used to form a non-woven include but are not limited to: a spunbond process, a meltblown process, a coform process, a hydro-entangled process, a through air bonded carded web process, a needle punched process, and an air-laid process. Desirably, a through air bonded carded web process is utilized.

The absorbent layer 22 can be a three-dimensional material having a length, a width and a thickness. Desirably, the absorbent layer 22 is a bulky fabric. By "bulky" it is meant that the absorbent layer 22 has a thickness ranging from between about 0.6 mm to about 6 mm. Desirably, the absorbent layer 22 has a thickness ranging from between about 1 mm to about 4 mm. More desirably, the absorbent layer 22 has a thickness ranging from between about 1 mm to about 3 mm. The absorbent layer 22 has a fabric component to which a binder, i.e. a liquid adhesive, and superabsorbent can be attached. These thickness ranges assumes that the fabric has a basis weight ranging from about 25 gsm to about 100 gsm with a bulk density ranging from between about 0.025 g/cc to about 0.05 g/cc, and a superabsorbent having a basis weight ranging from between about 100 gsm to about 1,000 gsm, with a bulk density ranging from between about 0.5 g/cc to about 0.9 g/cc.

The thickness of the absorbent layer 22, for the purpose of calculating density, is determined using the combined EDANA/INDA test procedure World Supply Partners (WSP) 120.6, formerly known as "EDANA Recommended Test (ERT) 30.5.99".

The absorbent layer 22 can be formed from various materials including a renewable material. By "renewable material" it is meant a material that can be renewed or replaced by new growth. The absorbent layer 22 can also be formed from materials that are biodegradable, biocompatible and/or compostable. Materials that work well for the absorbent layer 22 are those currently used to construct acquisition layers, also commonly referred to as acquisition/distribution layers, distribution layers and/or surge layers. Such an acquisition layer is commonly employed in a disposable absorbent article, such as baby and infant diapers, child care training pants, adult incontinent products, feminine napkins, pantyliners, etc. The fabric component of the absorbent layer 22 should allow fast penetration of body fluids, such as urine, blood, liquid feces, etc, downward therethrough in the z-direction. In addition, the fabric component of the absorbent layer 22 should allow the body fluid to disperse in a plane aligned parallel to the first surface 14 of the disposable waste containment article 10. Such a fabric, which forms a part of the absorbent layer 22, is generally characterized as being relatively open, having a low density fibrous structure with at least two different fiber sizes and a high surface area.

The absorbent layer 22 should have a density ranging from between about 0.05 grams/cubic centimeter (g/cc) to about 0.6 g/cc. Desirably, the absorbent layer 22 should have a density ranging from between about 0.07 g/cc to about 0.4 g/cc. More desirably, the absorbent layer 22 should have a density of less than about 0.03 g/cc. Even more desirably, the absorbent layer 22 should have a density ranging from between about 0.09 g/cc to about 0.3 g/cc.

The fabric component of the absorbent layer 22 should not only take in body fluid rapidly but should be able to minimize the escape of any superabsorbent that may be positioned in it, on it, or be attached to it. By constructing the fabric component of the absorbent layer 22 to have sufficiently small and tortuous pores in combination with a relatively large void volume, this can be accomplished. Furthermore, the fiber surface area in the fabric component of the absorbent layer 22 (i.e. low density/large void volume) should be greater than about 1,000 $cm^2/g$. This fiber surface area helps ensure that the escape of any superabsorbent, that is present, is minimized. Desirably, the fiber surface area in the fabric component of the absorbent layer 22 is greater than about 1,500 $cm^2/g$. More desirably, the fiber surface area in the fabric component of the absorbent layer 22 is greater than about 2,000 $cm^2/g$.

It should be understood that one skilled in the art can determine the surface area of fibers by the following method. For round fibers, the surface area is calculated using the formula $4/(D \times \rho)$, where fiber diameter D is in centimeters (cm) and density $\rho$ is in g/cc. In terms of denier d and density $\rho$, the formula is $3363/(d \times \rho)^{1/2}$.

The fabric component of the absorbent layer 22 also is a three-dimensional material having a length, a width and a thickness. Desirably, the fabric component is a bulky, non-woven fabric. The fabric component has a thickness ranging from between about 0.5 mm to about 5.9 mm. Desirably, the fabric component has a thickness ranging from between about 0.9 mm to about 3.9 mm. More desirably, the fabric component has a thickness ranging from between about 0.9 mm to about 2.9 mm. The fabric component should have a density of less than about 0.05 g/cc. Desirably, the fabric component should have a density of less than about 0.04 g/cc. More desirably, the fabric component should have a density of less than about 0.03 g/cc. Even more desirably, the fabric component should have a density of less than about 0.025 g/cc. The low density of the fabric component of the absorbent layer 22 permits body fluid to readily pass through the thickness of the fabric component and into contact with a superabsorbent 28.

The fiber surface areas within webs composed of modified cross-section fibers (i.e. non-round fiber), such as modified cross-section staple fibers or modified cross-section melt extruded fibers, or splitable fibers can be measured by the BET method of Brunauer, Emmett and Teller, published in the Journal of the American Chemical Society, 60, 309 (1938) and discussed in many textbooks dealing with material surfaces such as the 3$^{rd}$ addition of "Physical Chemistry of Surfaces" by Arthur W. Adamson, published by John Wiley & Sons, 1976, chapters XIII and XIV. This BET method is incorporated by reference in its entirety and made a part hereof.

The BET technique involves the absorption of a monomolecular layer of gas molecules onto the surface of the fibers. Calculations regarding the amount of gas present on the fibers yields a quantification of the fiber surface area values. This method has been used fairly routinely in the paper industry for fibrous webs, such as papers, fillers and filter materials.

The fabric component of the absorbent layer 22 should be somewhat compression resistant and should be relatively resilient. The fabric component of the absorbent layer 22 can be a through air bonded non-woven using bicomponent binder fibers of a first diameter joined to polyester fibers having a larger second diameter. The non-woven's bicomponent fibers can be constructed of, for example, a polyethylene sheath with a polypropylene core such that the sheath material has a lower melt temperature than the core material for effective thermal bonding. A hi-loft material of this type is commercially available from Shalag Industries Ltd., Kibbutz Shamir, Upper Galilee, Israel. This material is sold as STAPTE-35 and is a hi-loft non-woven web containing polyethylene/polyester bicomponent fibers or polyethylene/polypropylene bicomponent fibers and polyester staple fibers. Other suitable materials useful as the three-dimensional fabric 10 are taught in U.S. Pat. No. 5,562,650 to Everett et al., U.S. Pat. No. 5,490,846 to Ellis et al., U.S. Pat. No. 5,364,382 to Latimer, et al., U.S. Pat. No. 5,522,810 to Allen, et al., and U.S. Pat. No. 5,486,166 to Bishop et al. These patents are incorporated by reference and made a part hereof.

The fabric component of the absorbent layer 22 can also be constructed from fibers based on renewable resources, for example INGEO fiber produced by NatureWorks, LLC, of Minneapolis, Minn. Furthermore, the absorbent layer 22 can be constructed from recycled polymers, further improving the cost effectiveness and impact on the environment. By "recycled" it is meant to extract useful materials from waste; to put or pass through a cycle again; to extract and especially reprocess materials found in waste for reuse; to use again.

The absorbent layer 22 has an outer perimeter 24 which is approximately coincident with the outer perimeter 16 of the bodyside layer 12 and/or the outer perimeter 20 of the garment facing layer 18. Alternatively, the outer perimeter 24 of the absorbent layer 22 can be much smaller than the outer perimeters, 16 or 20 respectively, of the bodyside layer 12 and/or the garment facing layer 18. For example, the size and configuration of the absorbent layer 22 can allow the absorbent layer 22 to be completely enclosed and sandwiched between the bodyside layer 12 and the garment facing layer 18. Desirably, the outer perimeter 24 of the absorbent layer 22 is coincident with the outer perimeter 16 of the bodyside layer 12 and with the outer perimeter 20 of the garment facing layer 18, so that all three layers have the same size and configuration and can be easily bonded together, if desired.

The absorbent layer 22 also has a first major surface 26 which contains superabsorbent 28. The first major surface 26 faces towards the garment facing layer 18. The superabsorbent 28 can be attached to the first surface 26 by a liquid adhesive, not shown, or by any other means known to those skilled in the art. The liquid adhesive can be formed from various liquid based adhesives. One example of a liquid adhesive that works well is a sprayable, synthetic elastomer based polyurethane adhesive that is fast tacking, capable of low pressure spraying with minimal misting and cobwebbing, and that offer high coverage and a long bonding range. This liquid adhesive is FastBond 77, commercially sold by 3M Company of St. Paul, Minn. This liquid adhesive has low soak-in for long lasting bonds with high tack, high coverage and is fast drying. The liquid adhesive can be applied to the first surface 26 by being sprayed, being applied in droplet form, by being printed, by being atomized into tiny particles or a fine spray, by being mixed with pressurized air, etc. and directed toward the absorbent layer 22. By "spray" it is meant that the adhesive moves in a mass of dispersed droplets such as a fine jet of liquid discharged from a pressurized source.

Alternatively, an especially attractive printing method is, for example, "kiss" roll (i.e. transfer roll) printing wherein the "kiss" roll is partially submerged in the liquid adhesive and transfers the liquid adhesive from its surface to the fabric as the fabric passes over the rotating "kiss" roll. Methods of using this technique to apply materials in a non-continuous manner are known to those skilled in the art. In particular, the methods taught in U.S. Pat. Nos. 5,709,747; 5,885,656 and 6,183,847 wherein shields, shutters and raised areas are used for the non-continuous material application can also be used. Other printing methods, such as gravure printing, can also be used.

In general, any system of applying the liquid adhesive can be utilized so long as the adhesive remains liquid, for example flowable or deformable, for a given period of time. A superabsorbent 28 is then positioned or deposited onto the absorbent layer 22. The adhesive should remain in a liquid or semi-liquid state, or remain tacky for a short period of time to allow the superabsorbent 28 to adhere to it.

The superabsorbent 28 is a hydrogel or hydrocolloidal material. Desirably, the superabsorbent 28 is formed from one or more renewable materials. The superabsorbent 28 can also be formed from materials that are biodegradable, biocompatible and/or compostable. The superabsorbent 28 can be a cross-linked, solution or suspension polymerized, hydrogel forming material. The superabsorbent 28 can include at least some natural based materials. Commonly, the superabsorbent 28 contains synthetics or man made materials.

The superabsorbent 28 is normally added to the disposable waste containment article 10 to increase the amount of fluid which it can acquire and also to increase its fluid retention capabilities. The superabsorbent 28 can be in the form of individual particles, in powder form or in fiber form. Desirably, the superabsorbent 28 is in particle form. The superabsorbent 28, when in particle or fiber form, should not exhibit any sharp edges or corners. For example, the superabsorbent 28 when produced with a suspension polymerization process generally does not have sharp edges. If the superabsorbent 28 is produced with a solution polymerization process, the superabsorbent 28 can be treated or processed to remove any sharp edges or corners from the particles by methods known to those skilled in the art. This feature will help ensure that the superabsorbent 28 does not poke or form holes or openings in an adjacent layer, especially in the garment facing layer 18.

The superabsorbent 28 should be generally strong, stiff and have the ability to absorb body fluid under restraining forces resulting in a superabsorbent gel bed that remains permeable when the superabsorbent 28 is swollen. Various characteristics are known to those skilled in the art for qualifying desirable superabsorbents. The superabsorbent 28, when in particle form, should have an Absorbency Under Load (AUL) value measured at 0.6 psi of greater than about 13 grams/ grams (g/g). Desirably, the superabsorbent 28, when in particle form, should have an Absorbency Under Load (AUL) value measured at 0.6 psi of greater than about 20 grams/grams (g/g). More desirably, the superabsorbent 28, when in particle form, should have an Absorbency Under Load (AUL) value measured at 0.6 psi of greater than about 23 grams/grams (g/g). Even more desirably, the superabsorbent 28, when in particle form, should have an Absorbency Under Load (AUL) value measured at 0.6 psi of greater than about 25 grams/grams (g/g).

The superabsorbent 28, when in particle form, should be large enough to minimize passage of it through the absorbent layer 22 and small enough to minimize discomfort and damage to any adjacent layer. Therefore, at least about 98% of the superabsorbent 28, when in particle form, should range from between about 45 micrometers to about 840 micrometers. Desirably, the particles of the superabsorbent 28, should range from between about 65 micrometers to about 800 micrometers. More desirably, the particles of the superabsorbent 28 should range from between about 150 micrometers to about 600 micrometers. Even more desirably, the particles of the superabsorbent 28 should range from between about 200 micrometers to about 600 micrometers.

The particle size of a superabsorbent material, when in particle form, may be determined by sieve size analysis. A stack of sieves with different size openings may be used to determine the particle size distribution of a given sample. For example, in principle, a particle that is retained on a sieve with 600 micrometer openings is considered to have a particle size greater than 600 micrometers.

One way to determine the superabsorbent particle size is to use sieves having 841 (U.S. Sieve No. 20), 707 (U.S. Sieve No. 25), 595 (U.S. Sieve No. 30), 210 (U.S. Sieve No. 70), 149 (U.S. Sieve No. 100), 105 (U.S. Sieve No. 140) and 44 (U.S. Sieve No. 325) micrometer openings and placing them in order of the size of the openings with the largest openings on the top of the stack and the smallest openings on the bottom of the stack. The stack is placed on the top of a pan. A 25 gram to 100 gram sample of superabsorbent particles is then placed into the sieve with the largest openings. The sieve stack is shook for 10 minutes with a Ro-Tap Mechanical Sieve Shaker, Model B, available from W. S. Tyler of Mentor, Ohio, or other similar shaking device. After shaking is complete, the superabsorbent particles retained on each sieve are weighed and recorded. The weights retained on the different size sieves are divided by the initial sample weight to determine the percent superabsorbent retained on each sieve. If the sum of the superabsorbent passing through the larger sieve and retained on the smaller sieve is greater than about 98%, the particles are considered to be within the range of interest. For example, if greater than 98% of the superabsorbent passes through the U.S. Sieve No. 20 and is retained on the U.S. Sieve No. 325, for the purpose of this invention, it has a particle size between about 45 micrometers and 840 micrometers. Similarly, if greater than 98% of the superabsorbent passes through the U.S. Sieve No. 25 and is retained on the U.S. Sieve No. 140, for the purpose of this invention, it has a particle size between about 105 micrometers and 705 micrometers.

An example of a superabsorbent 28 that has been found to be suitable for this invention is Sanwet KC-770, produced by San-Dia Polymers, Ltd, Tokyo, Japan. An example of another superabsorbent believed to be suitable for this invention is Sanwet IM-930, also produced by San-Dia Polymers, Ltd. These particular superabsorbents are partially cross linked, solution polymerized sodium polyacrylate. Other suitable superabsorbents which have a more rounded and narrower particle size distribution include Aquapearl DS50TI, also produced by San-Dia Polymers, Ltd. and Aqua Keep SA55SX II, produced by Sumitomo Seika Chemicals Company, Ltd of Osaka, Japan. These last two superabsorbents are suspension polymerized, partially cross linked, sodium polyacrylate superabsorbents. Still other acceptable superabsorbents that can be used in this invention include superabsorbents available from BASF, Charlotte, N.C.; Degussa, Greensboro, N.C.; superabsorbents from Nippon Shokubai, Osaka, Japan; and superabsorbent fibers (SAF), e.g. sold as Oasis, by Technical Absorbents Ltd., Grimsby, United Kingdom. Still further, other suitable hydrogel forming materials include those beginning with natural based resources are available from various venders. SuperNatural Absorbing polymers (SNAPs) are manufactured by Archer Daniels Midland having an office in Decatur, Ill. Biocompatible, biodegradable polymers, such as those taught in U.S. Pat. No. 6,833,488, may be used. The teachings of U.S. Pat. No. 6,833,488 are incorporated by reference and made a part hereof.

The superabsorbent 28 can be applied to the absorbent layer 22 in various ways. These ways include, but are not limited to: being deposited, dropped by gravity, metered, blown, sifted, being applied using a vacuum or suction, or by other means known to those skilled in the art. The superabsorbent 28 can be homogenously applied to the absorbent layer 22 to create a uniform distribution of particles, powder or fibers in the machine-direction and/or in the cross-direction. Alternatively, the superabsorbent 28 can be applied in a non-uniform pattern onto the absorbent layer 22. Desirably, the superabsorbent 28 is deposited in particle form onto the absorbent layer 22 as the absorbent layer 22 is being advanced or moved in the machine direction. The superabsorbent 28 can be pulsed from a hopper using solenoid valves or other devices known to those skilled in the art. It should be understood that the superabsorbent 28 will adhere to the liquid adhesive that can be applied to the first major surface 26 of the absorbent layer 22.

Referring again to FIG. 1, the disposable waste containment article 10 further includes a seal 30 which bonds at least a portion of the bodyside layer 12 to the garment facing layer 18 and forms an internal volume 31. The internal volume 31 can range from between about 100 ml to about 2,000 ml. Desirably, the internal volume 31 will range from between about 200 ml to about 1,500 ml. More desirably, the internal volume 31 will range from between about 300 ml to about 1,200 ml. Even more desirably, the internal volume 31 will be about 1,000 ml or 1 liter. The internal volume 31 can expand as body waste enters the disposable waste containment article 10. It should be noted that the disposable waste containment article 10 can contain one or more folds, pleats, bellows, etc. (not shown) to allow it to expand. Alternatively, the bodyside layer 12 and/or the garment facing layer 18 may be made from extensible or elastic materials.

The seal 30 secures and bonds at least a portion of the bodyside layer 12, the garment facing layer 18 and the absorbent layer 22 together. More desirably, the seal 30 will bond each and every layer of the disposable waste containment article 10 together. Alternatively, the seal 30 can bond selected layers of the disposable waste containment article 10 together. The seal 30 is shown being positioned inward of the outer perimeters 16. The distance d that the seal 30 is located inward of the outer perimeter 16 can vary. Desirably, the distance d is equal to or greater than about 0.5 millimeters (mm). More desirably, the distance d is equal to or greater than about 1 mm. It should be noted that the distance d can vary depending upon the overall size and configuration of the disposable waste containment article 10 and the shape and position of the seal 30. Optionally, the seal 30 could extend to the outer perimeter 16, if desired. It has been found that when the seal 30 is located inward of the outer perimeter 16, that the edge of the disposable waste containment article 10 is softer. It is desirable to avoid making the edge of the disposable waste containment article 10 stiff, hard, abrasive or sharp because it may contact the inner thighs, legs or buttocks of a user during use. The disposable waste containment article 10 should be comfortable when being worn by a person.

The seal 30 can be formed by ultrasonics, by using heat, pressure, a combination of heat and pressure, by using glue, by using an adhesive, or by using any other type of sealing and/or bonding technique or materials known to those skilled in the art. The seal 30 can be a continuous line as is shown in FIG. 1. Alternatively, the seal 30 can be an intermittent line, a combination of a continuous and an intermittent line, two or more lines, etc. Desirably, the seal 30 will be a continuous line which extends completely around the disposable waste containment article 10. The seal 30 has a width w which can range from between about 1 millimeter (mm) to about 50 mm. Desirably, the width of the seal 30 will range from between about 1 mm to about 10 mm. More desirably, the width w of the seal 30 will range from between about 1 mm to about 5 mm.

The purpose of the seal 30 is to permit the bodyside layer 12 to remain attached to the garment facing layer 18 so that fluid or liquid, especially urine, and semi-solids and solid fecal matter can be captured and held therein. It should be understood that the disposable waste containment article 10 will be positioned over a single body orifice. Therefore, the disposable waste containment article 10 will accept body waste from only one orifice and therefore urine will not mix with fecal matter since each is voided from a human body through separate body orifices. The seal 30 should not prevent the bodyside layer 12 and the garment facing layer 18 from moving away from one another as body waste is received in the disposable waste containment article 10. However, the seal 30 is beneficial in preventing any body waste that has entered the disposable waste containment article 10 from leaking or seeping back out.

Still referring to FIGS. 1 and 2, the disposable waste containment article 10 also includes an ingress 32 that is formed in the bodyside layer 12. By "ingress" it is meant a means or place of entering. The ingress 32 extends completely through the bodyside layer 12 and is designed to be aligned with one of the waste orifices present in a human body. The ingress 32 is of sufficient size and dimensions to permit fluid, semi-solid and/or solid body waste discharged or expelled from a single orifice present in a human body to pass therethrough and be collected and retained in the disposable waste containment article 10.

The ingress 32 can be formed in any desired geometrical shape, including but not limited to: round, circular, oval, elliptical, square, rectangular, triangular, racetrack shape, etc. The ingress 32 can also vary in size but at a minimum, it should be large enough to completely span across the length and width of the waste orifice over which it is placed.

In FIGS. 1 and 2, the ingress 32 is depicted as an enlarged aperture 34 having a circular configuration with a minimum internal dimension $d_1$. In FIGS. 1 and 2, the minimum internal dimension $d_1$ is equal to the internal diameter. By "enlarged aperture" it is meant an opening equal to, and desirably larger than a waste orifice present in a human body over which the disposable waste containment article 10 will be positioned. The minimum internal dimension $d_1$ of the enlarged aperture 34 should be at least equal to the waste orifice which it surrounds. The enlarged aperture 34 has a minimum internal dimension $d_1$ which ranges from about 1 mm to about 100 mm. In the case of a female, the enlarged aperture 34 can surround the entire urogenital area. By "urogenital area" it is meant the area defined by the labia majora including the urethra and the vagina. The minimum internal dimension $d_1$ of the enlarged aperture 34 should be at least about 10 mm. Desirably, the minimum internal dimension $d_1$ of the enlarged aperture 34 is at least about 25 mm. More desirably, the minimum internal dimension $d_1$ of the enlarged aperture 34 is at least about 50 mm. Even more desirably, the minimum internal dimension $d_1$ of the enlarged aperture 34 is at least about 75 mm.

The ingress 32 should be of sufficient size and shape to completely surround and extend beyond one of the waste orifices present in the human body, yet not so large as to unnecessarily expose a large amount of the wearer's skin to the body waste inside of the disposable waste containment article 10. As explained above, in the case of a female, the ingress 32 could encompass the urogenital area. Desirably, the minimum internal dimension $d_1$ of the enlarged aperture 34 is at least about 1 mm larger than the waste orifice over which it is positioned during use, when the waste orifice is in an open position. More desirably, the minimum internal dimension $d_1$ of the enlarged aperture 34 is from between about 10 mm to about 100 mm larger than the waste orifice over which it is positioned during use, when the waste orifice is in an open position. Even more desirably, the minimum internal dimension $d_1$ of the enlarged aperture 34 is from between about 20 mm to about 75 mm larger than the waste orifice over which it is positioned during use, when the waste orifice is in an open position. Since the height, weight, and body shape of human beings varies greatly, the ingress 32 can be formed in different sizes to accommodate various individuals. For example, the anal orifice in an infant will be much smaller than the anal orifice in an adult.

It should be understood that if the enlarged aperture 34 is not circular or round but instead has some other geometrical configuration, than the minimum internal dimension $d_1$ of the enlarged aperture should be equal or larger than the waste orifice over which it is positioned during use, when the waste orifice is in an open position. Furthermore, in the case of a female, the enlarged aperture can surround the entire urogenital area.

Still referring to FIGS. 1 and 2, the disposable waste containment article 10 further includes an adhesive 36 secured to at least a portion of the first surface 14 of the bodyside layer 12. The adhesive 36 at least partially surrounds the ingress 32, and desirably, entirely surrounds the ingress 32. The adhesive 36 can be formed in any geometrical shape. In FIGS. 1 and 2, the adhesive 36 is shown as a circular ring having a width $w_1$. The width $w_1$ of the adhesive 36 can range from between about 1 mm to about 40 mm. Desirably, the width $w_1$ of the adhesive 36 can range from between about 5 mm to about 30 mm. More desirably, width $w_1$ of the adhesive 36 can range from between about 5 mm to about 25 mm. Even more desirably, width $w_1$ of the adhesive 36 can range from between about 10 mm to about 20 mm. The adhesive 36 also has an inner surface 38, an outer surface 40, an inner periphery 42 and an outer periphery 44. The inner surface 38 is secured to the first surface 14 of the bodyside layer 12 and the outer surface 40 is available for attachment to the skin of the wearer which surrounds the waste orifice. As mentioned above, the inner periphery 42 is of sufficient size to surround the waste orifice to which the disposable waste containment article 10 is to be positioned and desirably is larger so as to function properly.

The adhesive 36 is a body adhesive designed to be attached directly to the skin of a human body. Various kinds of body adhesives can be utilized and such body adhesives are well known to those skilled in the art. For example, the adhesive 36 can be a hydrogel and/or a hydrocolloid adhesive. Hydrogel and hydrocolloid adhesives are especially desirable in that they tend to swell when wetted, thereby ensuring non-leakage in the gasket area. The adhesive 36 can also be formed from materials that are biodegradable, biocompatible and/or compostable. The adhesive 36 has to be compatible with human skin in the urogenital and/or perianal areas of a human body. The adhesive 36 most likely will also contact body hair, especially in the crotch region. The adhesive 36 has to possess sufficient strength to secure the disposable waste containment article 10 to the human body as well as be able to be released or removed from the skin in a relatively comfortable manner. The adhesive 36 can be present in varying amounts. The adhesive 36 can be applied onto the first surface 14 of the bodyside layer 12 as an adhesive double coated woven, non-woven or film substrate, as a prefabricated adhesive film, as a coating, as a spray, as a slot coating, be brushed on, painted on, rolled on, dripped on, etc. These and other means for applying or securing the adhesive 36 onto the bodyside layer 12 are well known to those skilled in the art. The amount of adhesive 36 applied onto the bodyside layer 12 can range from between about 10 grams per square meter (gsm) to about 350 gsm. This amount should be sufficient for most applications depending upon the overall size and absorption capability of the disposable waste containment article 10. Desirably, the amount of adhesive 36 applied onto the bodyside layer 12 can range from between about 100 gsm to about 300 gsm when the adhesive is a hydrogel or hydrocolloid type adhesive. More desirably, the amount of adhesive 36 applied onto the bodyside layer 12 can range from between about 150 gsm to about 250 gsm when the adhesive is a hydrogel or hydrocolloid type adhesive. Even more desirably, the amount of adhesive 36 applied onto the bodyside layer 12 can range from between about 175 gsm to about 225 gsm when the adhesive is a hydrogel or hydrocolloid type adhesive.

Alternatively, when the adhesive 36 is a non-hydrogel pressure sensitive adhesive, for example, an acrylate adhesive, a lesser amount of adhesive may be sufficient. Desirably, when the adhesive 36 is a non-hydrogel pressure sensitive body adhesive, the amount of adhesive 36 applied to the bodyside layer 12 can range from between about 10 gsm to about 100 gsm. More desirably, when the adhesive 36 is a non-hydrogel pressure sensitive body adhesive, the amount of adhesive 36 applied to the bodyside layer 12 can range from between about 20 gsm to about 80 gsm.

It should also be understood that the amount of adhesive 36 applied to the bodyside layer 12 can be specified in terms of thickness, and one skilled in the art can readily calculate the equivalent amount of adhesive 36 that needs to be applied in terms of gsm.

Furthermore, if the adhesive 36 is in the form of an adhesive double coated substrate (a substrate coated on two opposing surfaces with an adhesive), then it is desirable that the substrate be breathable. The breathable feature can be obtained by using a material such as a porous or microporous film, a non-woven or a breathable fabric. Such a material is available from 3M Medical Specialties, St. Paul, Minn. under the designation Product Number 9917, 3M Double Coated Medical Tape.

Other examples of specific body adhesives that may be utilized include fiber reinforced acrylate based adhesive such as Product Number 1524, 3M Medical Transfer Adhesive, and hydrogel based adhesive Product Number 9880, 3M 18 mil Hydrogel Adhesive, both of which are available from 3M Medical Specialties, St. Paul, Minn. Another hydrogel adhesive that can be used is Product Number FW 656-222 available from First Water Limited, Wiltshire, United Kingdom.

An additional desirable feature of the body adhesive is that it be hypoallergenic, as is available in 3M adhesives, Product Numbers 9917 and 1524. The body adhesive can also be specifically designed for repeated skin contact as is the 3M adhesive, Product Number 9917.

Referring to FIG. 2, a removable release layer 46 is shown which is sized to overlie and cover the adhesive 36. The removable release layer 46 has an outer periphery 48 equal to or slightly larger than the outer periphery 44 of the adhesive 36. In FIG. 2, the removable release layer 46 is depicted as a disk although it could have any desired geometrical shape. For example, the removable release layer 46 could be formed as a circular ring. The release layer 46 functions to prevent the adhesive 36 from becoming contaminated prior to attachment of the disposable waste containment article 10 to the skin of a human body. Before the disposable waste containment article 10 is applied to a wearer's skin, the release layer 46 is removed and discarded. By keeping the adhesive 36 clean and free of any foreign substance, the adhesive 36 will be able to perform its intended function. One material that is suitable as the release layer 46 is as used in product FW 656-222, which contains a 40 micrometer, siliconized High Density Polyethylene (HDPE) commercially available from First Water Limited, Wiltshire, United Kingdom. The release layer 46 can also be formed from materials that are biodegradable, biocompatible and/or compostable.

Figure 3:
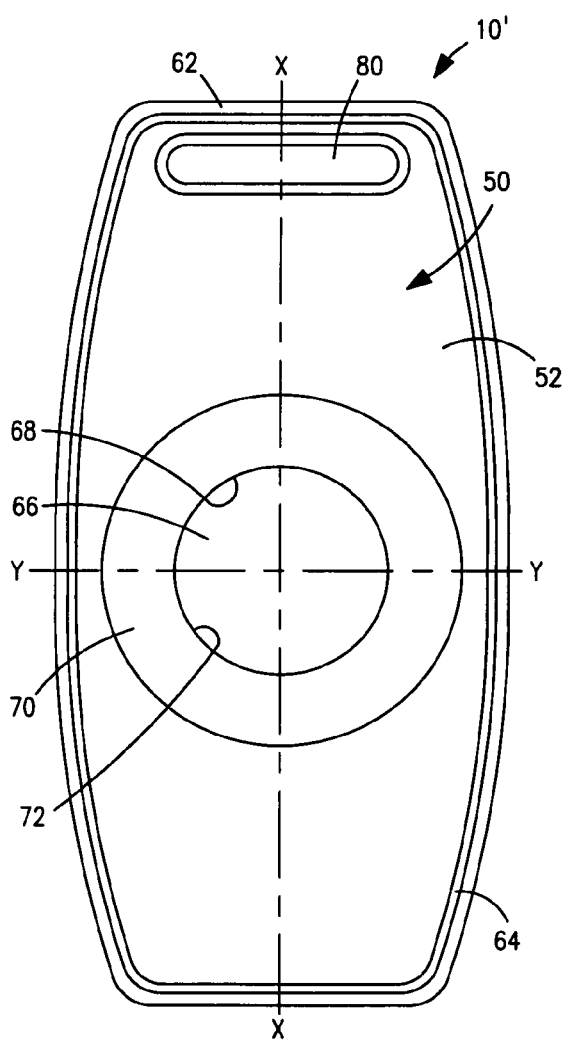
FIG. 3 is a front view of another embodiment of a disposable waste containment article designed to receive fecal matter and having an adhesive designed to be aligned with a waste orifice present in a human body and having a spaced apart adhesive sticker to provide extra holding power for retaining the disposable waste containment article to the wearer's skin.
Figure 4:
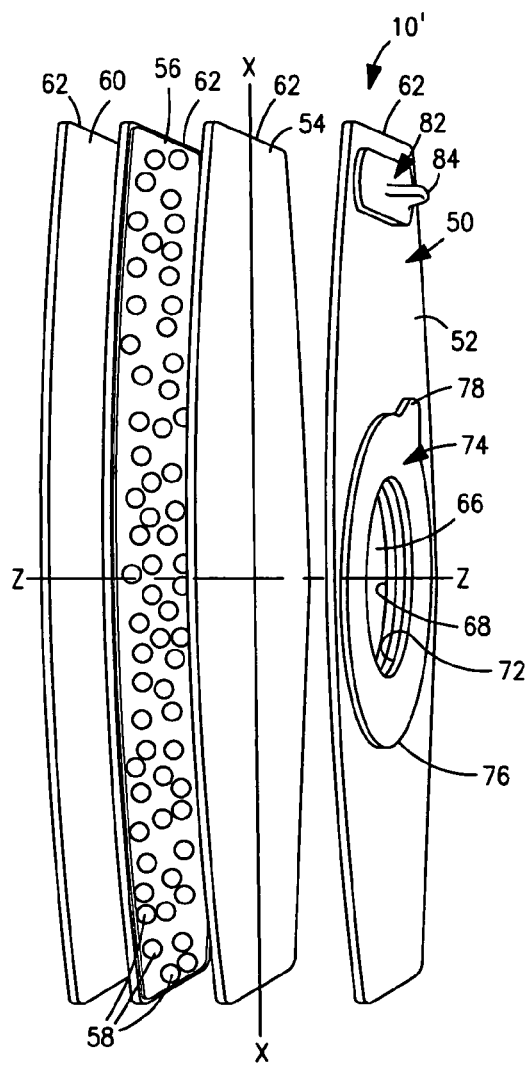
FIG. 4 is an exploded perspective view of the disposable waste containment article shown in FIG. 3 and showing a removable release layer overlying the adhesive.

Referring now to FIGS. 3 and 4, another embodiment of a disposable waste containment article 10' is shown. The disposable waste containment article 10' has a longitudinal central axis X-X, a transverse central axis Y-Y, see FIG. 3, and a vertical central axis Z-Z, see FIG. 4. The disposable waste containment article 10' is well suited for collecting excrement or fecal waste from a person's anus or anal orifice. The disposable waste containment article 10' includes a bodyside liquid-impermeable layer 50 having a first surface 52, an acquisition layer 54, an absorbent layer 56 containing superabsorbent 58, and a garment facing layer 60. It should be understood that the disposable waste containment article 10 or 10' can be constructed of three or more layers. For example, the disposable waste containment article 10 or 10' could include 3, 4, 5, 6, 7, 8, 9, 10 or more layers.

The acquisition layer 54, sometimes referred to as an acquisition/distribution layer, is located below the bodyside layer 50 to quickly distribute the body fluid in the x, y and/or z directions. The acquisition layer 54 can also be formed from materials that are biodegradable, biocompatible and/or compostable. The acquisition layer 54 is typically located above the absorbent layer 56 and is designed to acquire and retain any liquid body fluid or the liquid component of a semi-liquid body waste.

The absorbent layer 56, in addition to the previous discussion, is commonly constructed of cellulose material in fiber form, such as wood pulp fluff. The superabsorbent 58, as described above, is adhered to one surface of the absorbent layer 56 by a liquid adhesive or by other means known to those skilled in the art. Sometimes, a binder or binding fibers, such as bico bonding fiber, are added to assist in holding the absorbent layer 56 together and to retain the superabsorbent 58 in place. It should be understood that the superabsorbent, in particle, fiber or powder form, can also be interspersed in some of the pores of the absorbent layer 56, if desired. In FIG. 4, the superabsorbent 58 faces toward the acquisition layer 54 so as to be in an optimal position for absorbing any body fluid that enters the disposable waste containment article 10'. The garment facing layer 60 is located below the absorbent layer 56 and prevents body waste collected or absorbed in the disposable waste containment article 10' from exiting or seeping out therefrom.

Referring again to FIG. 3, each of the four layers 50, 54, 56 and 60 which form the disposable waste containment article 10' has an outer perimeter 62. A seal 64 is formed inward from this outer perimeter 62 and serves to secure or bind the four layers 50, 54, 56 and 60 together. The configuration, length, width, etc. of the seal 64 and the method used to form the seal 64 has been explained above with reference to FIGS. 1 and 2.

Still referring to FIGS. 3 and 4, the disposable waste containment article 10' further includes an enlarged aperture 66 formed through the bodyside layer 50 and approximate the transverse central axis Y-Y. The enlarged aperture 66 is sized and configured to be aligned with one of the waste orifices present in a human body, desirably the anus. Because of this, the enlarged aperture 66 is positioned approximately at the center of the disposable waste containment article 10'. The enlarged aperture 66 has an outer periphery 68. The enlarged aperture 66 provides a passageway through which liquid, semi-solid and solid waste from the anus can pass into the disposable waste containment article 10' and be collected and retained therein. In FIGS. 3 and 4, the enlarged aperture 66 is again depicted as a round or circular opening. The outer periphery 68 of the enlarged aperture 66 is at least partially surrounded, and desirably, entirely surrounded by a body adhesive 70. The body adhesive 70 is depicted as a circular ring of adhesive having an inner periphery 72. The body adhesive 70 can also be formed from materials that are biodegradable, biocompatible and/or compostable. The thickness and width of the body adhesive 70 can vary so long as a sufficient amount of body adhesive 70 is present to secure the disposable waste containment article 10' to the body of the wearer during use. The inner periphery 72 of the adhesive 70 can coincide with the outer periphery 68 of the enlarged aperture 66 or it can be made larger.

Referring to FIG. 4, the disposable waste containment article 10' also includes a removable release layer 74 which is sized to overlie and cover the body adhesive 70. The removable release layer 74 has an outer periphery 76 equal to or slightly larger than the outer periphery of the body adhesive 70. In FIG. 4, the removable release layer 74 is depicted as a circular ring, although it could have any desired geometrical shape. The release layer 74 functions to prevent the body adhesive 70 from becoming contaminated prior to attachment of the disposable waste containment article 10' to the skin of a human body. The removable release layer 74 also has a finger tab 78, which extends outward therefrom, and which can be used by the wearer or by a caregiver to separate the release layer 74 from the body adhesive 70. Before the disposable waste containment article 10' is applied to a wearer's skin, the release layer 74 is removed and discarded. By keeping the body adhesive 70 clean and free of any foreign substance, the body adhesive 70 will be able to perform its intended function. The release layer 74 can also be formed from materials that are biodegradable, biocompatible and/or compostable.

The disposable waste containment article 10' is also depicted as having a zone of adhesive 80 spaced apart from the body adhesive 70. The zone of adhesive 80 is also a body adhesive and facilitates holding and securing the disposable waste containment article 10' to the wearer's body. To prevent contamination prior to using the disposable waste containment article 10', the adhesive 80 is overlaid or covered by a removable release layer 82, see FIG. 4. As mentioned above in reference to the removable release layer 74, the removable release layer 82 can include a finger tab 84. The finger tab 84 extends outward from the removable release layer 82. The finger tab 84 can be removed by the wearer or by a caregiver to separate the release layer 82 from the body adhesive 70. Before the disposable waste containment article 10' is applied to a wearer's skin, the release layer 82 is removed and discarded. By keeping the zone of adhesive 80 clean and free of any foreign substance, the body adhesive 80 will be able to perform its intended function. The adhesive 80 and the release layer 82 can also be formed from materials that are biodegradable, biocompatible and/or compostable.

Referring to FIGS. 5 and 6, still another embodiment of a disposable waste containment article 10" is shown. The disposable waste containment article 10" has a longitudinal central axis X-X, a transverse central axis Y-Y, see FIG. 5, and a vertical central axis Z-Z, see FIG. 6. The disposable waste containment article 10" is well suited for collecting urine from a male. The disposable waste containment article 10" includes a five layer structure, although a fewer or a greater number of layers can be used, if desired. The five layers, from top to bottom, include a bodyside liquid-impermeable layer 86 having a first surface 88, an optional protection layer 90 to minimize contact between the penis and the liquid-impermeable layer 86, a first absorbent layer 92 having a first major surface 94 with superabsorbent 96 positioned thereon, a second absorbent layer 98 having a first major surface 100 with superabsorbent 102 positioned thereon, and a garment facing surface 104. The first major surface 94 of the first absorbent layer 92 faces towards the first major surface 100 of the second absorbent 98. Both of the first and second absorbent layers, 92 and 98 respectively, are separated from the bodyside layer 86 by the optional protection layer 90. The purpose of each layer 86, 90, 92, 98 and 104 is as described above and each layer 86, 90, 92, 98 and 104 can also be formed from materials that are biodegradable, biocompatible and/or compostable.

Each of the first and second major surfaces, 94 and 100 respectively, has a superabsorbent free zone 106, 108 that extends from between about 50% to 100% of the length l of each of the first and second absorbent layers, 92 and 98 respectively. Desirably, each of the superabsorbent free zones 106, 108 extends from between about 60% to about 95% of the length l of each of the first and second absorbent layers, 92 and 98 respectively. More desirably, each of the superabsorbent free zones 106, 108 extends from between about 75% to about 90% of the length l of each of the first and second absorbent layers, 92 and 98 respectively. Each of the superabsorbent free zones 106, 108 has a width $w_2$ of at least about 1 mm, desirably a width $w_2$ of at least about 2 mm, and more desirably, a width $w_2$ of at least about 5 mm.

Referring to FIG. 5, each of the five layers 86, 90, 92, 98 and 104, which form the disposable waste containment article 10", has an outer perimeter 110. A seal 112 is formed inward from this outer perimeter 110 and serves to secure or bind the five layers 86, 90, 92, 98 and 104 together. The configuration, length, width, etc of the seal 112 and the method used to form the seal 112 has been explained above with reference to FIGS. 1 and 2.

Still referring to FIGS. 5 and 6, the disposable waste containment article 10" further includes an ingress 114 formed through the bodyside layer 86. The ingress 114 is spaced away from the transverse central axis Y-Y and towards one end of the disposable waste containment article 10". The ingress 114 is depicted as two intersecting cuts or slits 116 and 118 formed in the bodyside layer 86. The two cuts 116 and 118 can be aligned at right angles (90 degrees) to one another or they can be aligned at some other angle. Each of the two cuts 116 and 118 can have a length ranging from between about 20 mm to about 100 mm. Desirably, each of the two cuts 116 and 118 can have a length $l_1$ ranging from between about 30 mm to about 60 mm. More desirably, each of the two cuts 116 and 118 can have a length $l_1$ ranging from between about 40 mm to about 50 mm. A length $l_1$ of about 45 mm works very well. It should be noted that each of the two cuts 116 and 118 can have a different length, if desired. The cuts 116 and 118 allow a male penis to be inserted into and through the ingress 114 formed through the bodyside layer 86. This design helps ensure that urine expelled through the penis is captured in the disposable waste containment article 10".

Referring to FIG. 7, an alternative embodiment of an ingress 114' is shown which can be formed in the disposable waste containment article 10". In this embodiment, the ingress 114' is depicted as having three slits 120, 122 and 124 emanating from a point 126. The ingress 114' is formed through the bodyside layer 86. The three slits 120, 122 and 124 are spaced approximately 120 degrees apart from one another. It should be understood that more than three slits can be employed and the spacing between adjacent slits can vary. Each of the slits 120, 122 and 124 has a length $l_2$ ranging from between about 10 mm to about 50 mm. Desirably, each of the slits 120, 122 and 124 has a length $l_2$ ranging from between about 15 mm to about 30 mm. More desirably, each of the slits 120, 122 and 124 has a length $l_2$ ranging from between about 20 mm to about 25 mm. A length $l_2$ of about 22 mm works very well. It should be noted that each of the slits 120, 122 and 124 can have a different length, if desired. The slits 120, 122 and 124 allow a male penis to be inserted into and through the ingress 114' formed through the bodyside layer 86. This design helps ensure that urine expelled through the penis is captured in the disposable waste containment article 10" and is retained therein.

Referring again to FIGS. 5 and 6, the disposable waste containment article 10" also contains a body adhesive (not shown) located around the ingress 114. The body adhesive is positioned about the ingress 114 in a similar fashion as was described with reference to FIGS. 1-4. The thickness and width of the body adhesive can vary so long as a sufficient amount of body adhesive is present to secure the disposable waste containment article 10" to the body of the wearer during use. A removable release layer 128 overlays and covers the body adhesive. The removable release layer 128 is in the configuration of a circular ring having an inner periphery 130, an outer periphery 132, and an optional slit 134. The inner periphery 130 is sufficiently large to surround the ingress 114 and allow a male penis to be inserted through it. In FIG. 6, a male penis 136 is shown being inserted through the inner periphery 130 of the removable release layer 128 and through the ingress 114. A scrotum 138 is positioned outside of the disposable waste containment article 10". By "scrotum" it is meant an external sac of skin enclosing the testes. It should be understood that through use of other ingress designs, such as described in FIGS. 1-4 and in FIGS. 8 and 9 below, the scrotum 138 could alternatively be placed inside the disposable waste containment article 10".

The optional slit 134, formed in the removable release layer 128, facilitates removal of the release layer 128 after the male penis 136 has been inserted into the ingress 114. The removable release layer 128 further includes a finger tab 140 which can be used to remove the release layer 128 from the body adhesive. By leaving the release layer 128 in place until the male penis 136 is inserted into the ingress 114, one may find that it is easier to correctly position and secure the disposable waste containment article 10" in a most advantageous position on the human body. The removable release layer 128 can also be formed from materials that are biodegradable, biocompatible and/or compostable.

Referring again to FIG. 5, one will see that another removable release layer 142 having a finger tab 144 is also secured to the opposite end of the disposable waste containment article 10". The removable release layer 142 overlies and covers another zone of adhesive (not shown) but which is similar to the adhesive zone 80, shown in FIG. 3. The adhesive zone can be used to help secure the disposable waste containment article 10" to the wearer's body. The removable release layer 142 can also be formed from materials that are biodegradable, biocompatible and/or compostable.

Figure 8:
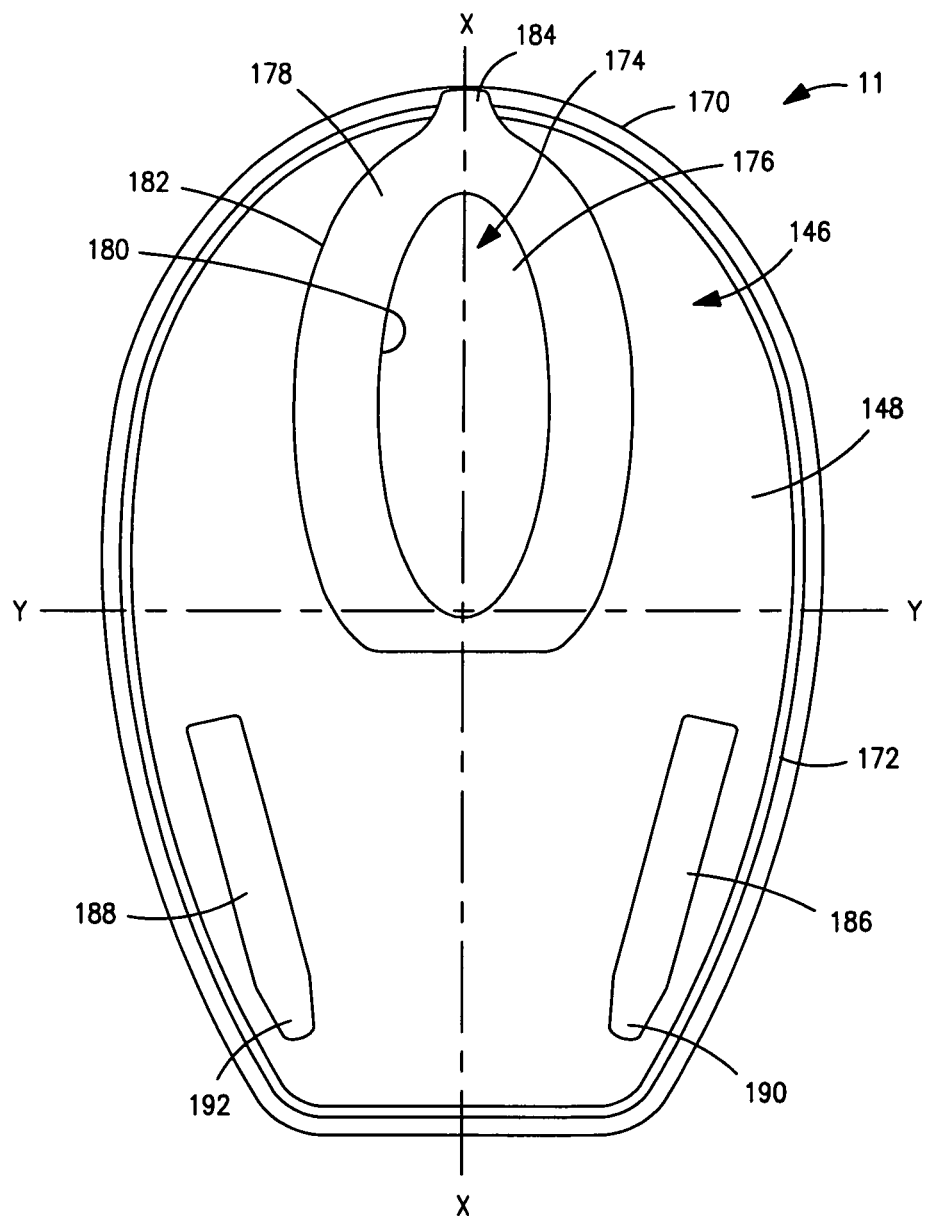
FIG. 8 is still another embodiment of a disposable waste containment article designed to receive urine from a female and having an oval shaped aperture.
Figure 9:
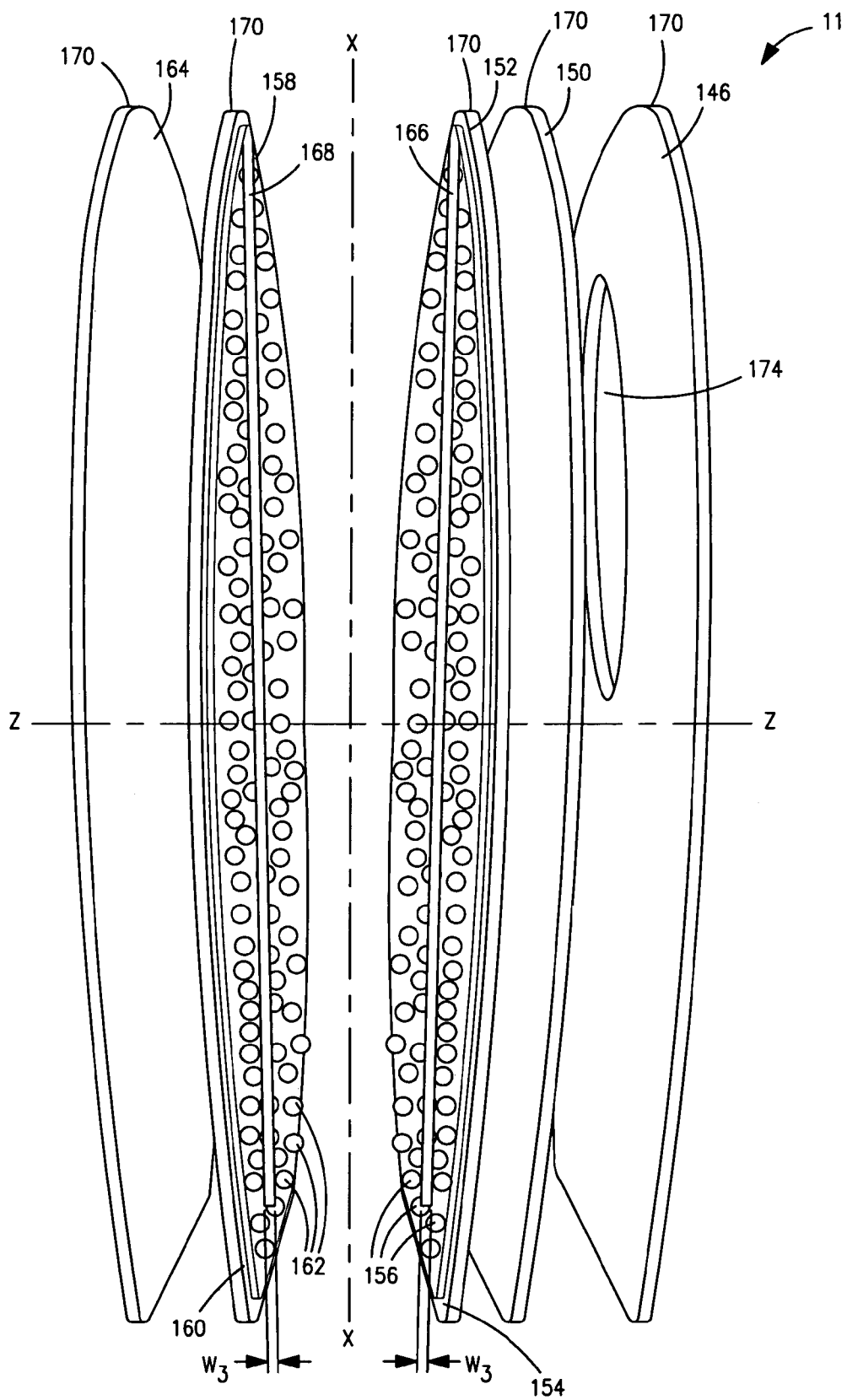
FIG. 9 is an exploded perspective view of the disposable waste containment article shown in FIG. 8 and depicting five separate layers.

Referring now to FIGS. 8 and 9, still another embodiment of a disposable waste containment article 11 is shown. The disposable waste containment article 11 has a longitudinal central axis X-X, a transverse central axis Y-Y, see FIG. 8, and a vertical central axis Z-Z, see FIG. 9. The disposable waste containment article 11 is well suited for collecting urine from a female's urethra. The disposable waste containment article 11 includes a five layer structure, although a fewer or a greater number of layers can be used, if desired. The five layers, from right to left, include a bodyside liquid-impermeable layer 146 having a first surface 148, see FIG. 8, an acquisition layer 150, a first absorbent layer 152 having a first major surface 154 with superabsorbent 156 positioned thereon, a second absorbent layer 158 having a first major surface 160 with superabsorbent 162 positioned thereon, and a garment facing layer 164. The first major surface 154 of the first absorbent layer 152 faces towards the first major surface 160 of the second absorbent 158. Both of the first and second absorbent layers, 152 and 158 respectively, are separated from the bodyside layer 146 by the acquisition layer 150. The purpose of each layer 146, 150, 152, 158 and 164 is as described above and each layer 146, 150, 152, 158 and 164 can also be formed from materials that are biodegradable, biocompatible and/or compostable.

Each of the first and second major surfaces, 154 and 160 respectively, has a superabsorbent free zone 166, 168 that extends from between about 50% to 100% of the length $l_3$ of each of the first and second absorbent layers, 152 and 158 respectively. Desirably, each of the superabsorbent free zones 166, 168 extends from between about 60% to about 95% of the length $l_3$ of each of the first and second absorbent layers, 152 and 158 respectively. More desirably, each of the superabsorbent free zones 166, 168 extends from between about 75% to about 90% of the length $l_3$ of each of the first and second absorbent layers, 152 and 158 respectively. Each of the superabsorbent free zones 166, 168 has a width $w_3$ of at least about 1 mm, desirably a width $w_3$ of at least about 2 mm, and more desirably, a width $w_3$ of at least about 5 mm.

Referring to FIG. 9, each of the five layers 146, 150, 152, 158 and 164 which form the disposable waste containment article 11 has an outer perimeter 170. A seal 172 is formed inward from this outer perimeter 170 and serves to secure or bind the five layers 146, 150, 152, 158 and 164 together. The configuration, length, width, etc of the seal 172 and the method used to form the seal 172 has been explained above with reference to FIGS. 1 and 2.

Still referring to FIGS. 8 and 9, the disposable waste containment article 11 further includes an ingress 174 formed through the bodyside layer 146. The ingress 174 is situated towards one end of the disposable waste containment article 11. The ingress 174 is depicted as an elongated, oval shaped aperture 176 having its longest dimension aligned along the longitudinal central axis X-X and its shortest dimension aligned along the transverse central axis Y-Y. This elongated, oval shaped aperture 176 helps ensure that urine expelled through the urethra and/or menses expelled through the vagina of a female are captured in the disposable waste containment article 11. The inner periphery of the oval shaped aperture 176 should be sufficiently large to surround both the female urethra and vagina. Expressed another way, the inner periphery of the oval shaped aperture 176 should be sufficiently large to surround the female's urogenital area.

The disposable waste containment article 11 also contains a body adhesive (not shown) located around the ingress 174. The body adhesive is positioned about the ingress 174 in a similar fashion as was described with reference to FIGS. 1-7. The thickness and width of the body adhesive can vary so long as a sufficient amount of body adhesive is present to secure the disposable waste containment article 11 to the body of the wearer during use. A removable release layer 178 overlays and covers the body adhesive. The removable release layer 178 is configured as an elongated oval ring having an inner periphery 180 and an outer periphery 182. The inner periphery 180 is sufficiently large to surround the ingress 174 and also surround the female's urogenital area. The outer periphery 182 is large enough and the inner periphery 180 is small enough to ensure coverage of the body adhesive. The body adhesive and the release layer 178 can also be formed from materials that are biodegradable, biocompatible and/or compostable.

No slit 134 is present in this embodiment. The removable release layer 178 further includes a finger tab 184 which can be used to remove the release layer 178 from the body adhesive.

Referring again to FIG. 8, one will see that two additional removable release layers 186 and 188, each having a finger tab 190 and 192 respectively, are also secured to the opposite end of the disposable waste containment article 11. Each of the removable release layers 186 and 188 overlies and covers a separate and distinct zone of body adhesive (not shown). However, each of the zones of body adhesive is similar to the body adhesive zone 80. The body adhesive zone can be used to help secure the disposable waste containment article 11 to the wearer's body. The removable release layers 186 and 188 and the body adhesive can also be formed from materials that are biodegradable, biocompatible and/or compostable.

Figure 10:
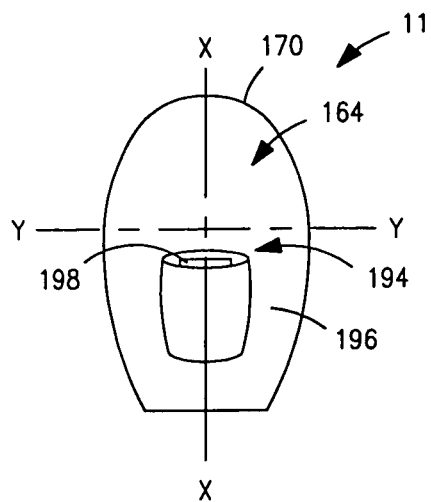
FIG. 10 is a plan view of the exterior surface of a garment facing layer having a pocket formed therein for holding a wipe.

Referring now to FIG. 10, the garment facing layer 164 is shown having an optional pocket 194 formed on an exterior surface 196 thereof. The pocket 194 is sized and shaped to be able to hold a wipe 198. The wipe 198 can be either a wet wipe or a dry wipe. The wipe 198 can be used to clean the skin of the wearer and/or the waste orifice before the disposable waste containment article 10, 10', 10" or 11 is attached or after it has been removed from the wearer's body.

Three different configurations of the disposable waste containment articles 10', 10" and 11, (Feces, Male Urine and Female Urine/Menses) were constructed according to the above teachings and are listed in the following Tables 1-3. The finished outside dimensions of each article was nominally 12 centimeters (cm) wide, nominally 27 cm long and nominally 3 mm thick. Each article varied in configuration as appropriate for its specific end use. The materials and quantities of each are listed in the Tables.

TABLE 1

Fecal

| Part | Material | QTY. |
|---|---|---|
| Apertured adhesive gasket | FW656-222 by First Water | 1 |
| Fastening sticker | FW656-222 by First Water | 1 |

TABLE 1-continued

Fecal

| Part | Material | QTY. |
|---|---|---|
| Apertured external layer | HUGGIES Outer Barrier Material | 1 |
| Acquisition layer | STAPTE-35 by Shalag | 1 |
| Absorption layer | STAPTE-35 w/Sanwet-770 SAP | 1 |
| External layer | HUGGIES Outer Barrier Material | 1 |

TABLE 2

Male Urine

| Part | Material | QTY. |
|---|---|---|
| Apertured adhesive gasket | FW656-222 by First Water | 1 |
| Fastening sticker | FW656-222 by First Water | 2 |
| Apertured external layer | HUGGIES Outer Barrier Material | 1 |
| Protection layer | STAPTE-35 by Shalag | 1 |
| Acquisition layer | STAPTE-35 by Shalag | 1 |
| Absorption layers | STAPTE-35 w/Sanwet-770 SAP | 2 |
| External layer | HUGGIES Outer Barrier Material | 1 |

TABLE 3

Female Urine/Menses

| Part | Material | QTY. |
|---|---|---|
| Apertured adhesive gasket | FW656-222 by First Water | 1 |
| Fastening stickers | FW656-222 by First Water | 2 |
| Apertured external layer | HUGGIES Outer Barrier Material | 1 |
| Acquisition layer | STAPTE-35 by Shalag | 1 |
| Absorption layers | STAPTE-35 w/Sanwet-770 SAP | 2 |
| External layer | HUGGIES Outer Barrier Material | 1 |

Each of the above disposable waste containment articles 10', 10" and 11 was used by adults with the following results.

After some experimentation all three disposable waste containment articles 10', 10" and 11 could easily be put on by the wearer or a caregiver. There was little to no sensation of the disposable waste containment articles 10', 10" and 11 being present and the wearer's motion was not hindered when the articles were worn along with elastic net support pants. In no cases was there any fluid leakage, even with an estimated 750 millimeters (ml) urine load and when urinating or defecating while the wearer was sitting and lying on his or her back. Removal of the body adhesive was pain free and without discomfort. The skin in the ingress area did not feel wet and the acquisition layer felt dry after use. Clean up after defecating was easy and disposal of the disposable waste containment articles 10', 10" and 11 was simple. The body adhesive, surrounding the enlarged aperture, was used to seal off or close the entrance to the filled disposable waste containment article 10', 10" and 11. Alternatively, the user placed the soiled disposable waste containment article 10', 10" and 11 in a resealable disposable pouch or bag. The pouch or bag was supplied to the user along with the disposable waste containment article 10', 10" and 11. There was very little odor noticed during wearing, use or disposal of the disposable waste containment articles 10', 10" and 11.

From the above, it can be seen that the disposable waste containment articles 10', 10" and 11 functioned well, were easy to use, and were comfortable.

Due to the effectiveness of the method of attaching the superabsorbent 28, 58, 96, 102 and 156 to the absorbent layer 22, 56, 92, 98 and 152 respectively, the amount of superabsorbent 28, 58, 96, 102 and 156 used ((5 grams (g) to 40 g; 15 g to 30 g; or even 20 g to 25 g)), the pattern of attaching the superabsorbent 28, 58, 96, 102 and 156 (with channels/voids), the interaction of the absorbent layer 22, 56, 92, 98 and 152 with the superabsorbent 28, 58, 96, 102 and 156, how the absorbent layer 22, 56, 92, 98 and 152 is positioned in the disposable waste containment articles 10', 10" and 11 (fastened to the perimeter), and the size of the disposable waste containment articles 10', 10" and 11 (for example, the interior volume space including possible expansion due to folding and/or use of extendable outer layers inside perimeter seals 64, 112 and 172, of 100 ml to 2,000 ml; 600 ml to 1,500 ml; or even 700 ml to 1,200 ml), performance was significantly improved over the prior art.

The amount of superabsorbent 28, 58, 96, 102 and 156 and the overall size of the disposable waste containment article 10', 10" or 11 can vary depending upon the physical anatomy of the person wearing the article. For example, an infant would require a smaller size article than a toddler or an adult. Likewise, an adult most likely would void a greater volume of urine and/or fecal matter than an infant or toddler.

The disposable waste containment articles 10', 10" and 11 are much more suitable for use in institutions and on those individuals with severe incontinence than any current commercial product. The disposable waste containment articles 10', 10" and 11 are also useful for the general public which has a desire for such products. For example, the disposable waste containment articles 10', 10" and 11 could be used by those who have a need to extend the time between using conventional toilet facilities such as astronauts, long-haul truckers and similar individuals.

Due to the ability of the disposable waste containment articles 10', 10" and 11 in preventing contact between urine and feces, skin health is promoted. Urease, an enzyme that promotes the hydrolysis of urea from bacteria in fecal material is prevented from acting on the urea in the urine thus reducing or eliminating ammonia formation. This allows for the maintenance of a healthier pH in the vicinity of the user's skin and reduces ammonia odor generation.

Figure 11:
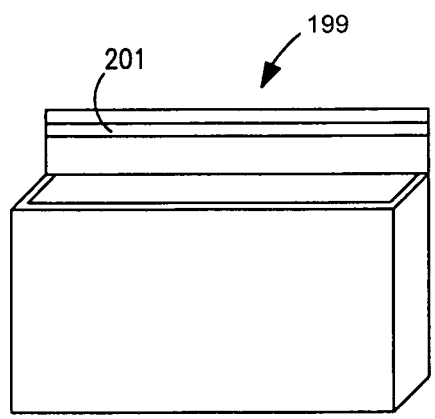
FIG. 11 is a perspective view of a pouch or bag having a resealable cover and which can retain a disposable waste containment article.

Referring to FIG. 11, each of the disposable waste containment articles 10', 10" and 11 may be delivered to the user in a sealable, moisture barrier type pouch or bag 199. The pouch or bag 199 can be formed from various materials known to those skilled in the art. The pouch or bag 199 desirably is formed from a thin flexible material that is easy to manufacture and assemble. Polyolefin films, such as polyethylene film and polypropylene film, work well. Alternatively, the pouch or bag 199 could be made to be resealable so as to dispose of a soiled waste containment article 10', 10" and 11 in a proper manner. The user's skin or the skin of a caregiver should avoid contact with the excrement or urine so as to prevent contamination. The pouch or bag 199 can be sealed using well known, commercially available closure systems known to those skilled in the art. Examples of closure systems include adhesives and glues, as well as mechanical systems, such as ZIPLOCK, VELCRO, etc. In FIG. 11, the pouch or bag 199 is capable of being sealed by a strip of adhesive 201 located on the inner surface of the flap.

The pouch or bag 199 can be sealed to insure freshness, prevent contamination with moisture, germs, bacteria, etc. The pouch or bag 199 can also be used to dispose of a disposable waste containment articles 10', 10" and 11 after it has been used, soiled and/or removed from the human body. The individual disposable waste containment articles 10', 10" and 11 can be initially sealed in the resealable pouch or bag 199 and several such pouches or bags 199 can be assembled into a larger package (not shown), for example, two or more per package, according to marketing requirements.

Referring to FIGS. 12 and 13, an alternative arrangement for attaching a disposable waste containment article is shown. As stated above, the disposable waste containment article is capable of collecting body waste from one of the waste orifices present in a human body. The alternative arrangement includes using a sticker 200 which is applied directly to the skin of a human body. The sticker 200 can stay in place for a number of days, without causing irritation to the wearer. The sticker 200 is made of non-toxic ingredients and can also be formed from materials that are biodegradable, biocompatible and/or compostable. Desirably, the sticker 200 is formed from a breathable material. The sticker 200 should be non-irritating. The sticker 200 can be hypo-allergenic, if desired. Furthermore, the sticker 200 can be waterproof.

The sticker 200 is anatomically shaped to be positioned about one of the waste orifices present in the human body. The sticker 200 can be specifically sized and configured to accommodate the anal orifice, the male urethral orifice, or the female urethral orifice. The sticker 200 should be flexible and easy to apply to maximize comfort to the wearer.

Referring to FIG. 13, the sticker 200 is specifically configured to surround an anal cavity. The sticker 200 has a first member 202 with a first major surface 204, a second major surface 206, and a body adhesive 208 secured to the first major surface 204. The second major surface 206 is formed from a material having a texture that allows for the repeated attachment and removal of corresponding collection receptacles. As shown in FIG. 12, the sticker 200 has an aperture 210 formed therethrough. Desirably, the aperture 210 is round or circular in configuration and has a sufficient diameter to completely surround the anus. The sticker 200 also has an inner periphery 212 and an outer periphery 214. The body adhesive 208 allows the sticker 200 to be removably attached to a human body such that the inner periphery 212 surrounds one of the waste orifices. The body adhesive 208 can be constructed to be temperature-sensitive so that it can be removed from the human body by applying a damp, cold or wet towel to the sticker 200. The body adhesive 208 should also be formulated such that it is effective for use over a period of several days.

A release layer 216 is removably secured to the body adhesive 208. The release layer 216 can optionally include a finger tab 218 which facilitates removal of the release layer 216 from the body adhesive 208. The release layer 216 prevents the body adhesive 208 from becoming contaminated prior to attachment of the sticker 200 to the human body. The release layer 216 and the body adhesive 208 can also be formed from materials that are biodegradable, biocompatible and/or compostable.

Referring to FIG. 14, a disposable collection receptacle 220 can be secured to the sticker 200 so as to be positioned about one of the waste orifices present in a human body. The disposable collection receptacle 220 contains a fluid absorbing material (not shown). The receptacle 220 has an opening 222 formed therein which is at least partially surrounded by a first adhesive 224. The opening 222 has an inner periphery 226 sized and configured to correspond with the inner periphery 212 of the sticker 200. The first adhesive 224 is designed to adhere to the second major surface 206 of the sticker 200. In FIG. 14, a removable release layer 228 initially covers the first adhesive 224 and is designed to be removed prior to securing the disposable collection receptacle 220 to the sticker 200. Like the release layer 216, the release layer 228 prevents the first adhesive 224 from becoming contaminated prior to attachment of the disposable collection receptacle 220 to the second major surface 206 of the sticker 200. The release layer 228 can include a finger tab 230 to assist in lifting and removing the release layer 228 from the first adhesive 224. The receptacle 220 can also be formed from materials that are biodegradable, biocompatible and/or compostable.

It should be understood that the disposable collection receptacle 220 can optionally contain an odor absorbing material as well.

Referring to FIG. 15, another embodiment of a sticker 200' is shown which is specifically designed to be secured about the urethral opening of a female. The sticker 200' has an elongated aperture or opening 210' having an inner periphery 212'. The shape of the aperture 210' is suited to better accommodate the shape of a woman's urethra and vagina and will also encompass her entire urogenital opening. The sticker 200' can also be formed from materials that are biodegradable, biocompatible and/or compostable.

Referring to FIG. 16, still another embodiment of a sticker 200" is shown which is specifically designed to be secured to a male penis. The sticker 200" is designed to be placed over the wearer's penis. The sticker 200" has a round or circular aperture 210" with an enlarged inner periphery 212". The body adhesive 208 is designed to be initially covered by a removable release layer (not shown) which can optionally include a finger tab to assist in its removal from the body adhesive 208. The sticker 200" can also be formed from materials that are biodegradable, biocompatible and/or compostable.

Referring to FIG. 17, a male urine collection receptacle 232 is shown. The male urine collection receptacle 232 is depicted as an elastic sheath that is placed over the wearer's penis so as to direct all urine to pass straight into the urine collection receptacle 232. The male urine collection receptacle 232 is removably attached to the male sticker 200" by affixing a first adhesive 234 formed on the male urine collection receptacle 232 to the male sticker 200". The first adhesive 234 can be initially covered by a removable release layer, not shown, but which functions in a similar fashion to the release layer 216, described above. The male urine collection receptacle 232 should include a liquid absorbing material (not shown) in order to absorb and collect urine. The absorbing material can use chemicals or involve chemical processes currently known to those skilled in the art in order to absorb, solidify, or otherwise capture the urine. The male urine collection receptacle 232 can optionally be equipped with a unidirectional valve to prevent urine from exiting the receptacle 232. The male urine collection receptacle 232 can also be formed from materials that are biodegradable, biocompatible and/or compostable.

When the wearer urinates, the waste matter passes from the body, through the opening 210" in the male sticker 200" and directly into the male urine collection receptacle 232, where it remains until the urine male collection receptacle 232 is detached from the male sticker 200" and discarded.

Individual fecal and urine collection receptacles 220 and 232 can be attach to the stickers 200, 200' and 200". Each collection receptacle 220 and 232 is a sealed, disposable container that receives and stores waste matter. These collection receptacles 220 and 232 are designed to be disposed of as needed. The collection receptacles 220 and 232 sit in the undergarment or diaper of the wearer. There is the option to temporarily connect the collection receptacles 220 and/or 232 to the undergarments of the wearer, if desired.

All embodiments of the urine collection receptacles 220 and 232 contain moisture-absorbing material in order to contain the urine and further aid in preventing fluid leakage. Odor absorbent materials can also be included in the collection receptacles 220 and 232.

The urine and fecal collection receptacles 220 may optionally be joined such that they function as a single unit with separate compartments.

A fecal collection receptacle 220, as shown in FIG. 13, functions to collect fecal matter expelled by a male or female wearer. The fecal collection receptacle 220 is a sealed container that can optionally contain odor absorbent materials. The opening 222 formed in the fecal collection receptacle 220 corresponds to the opening 210 formed in the anal sticker 200. The fecal collection receptacle 220 is removably attached to the anal sticker 200 by aligning the two openings 210 and 222 and affixing a first adhesive 224 on the fecal collection receptacle 220 to the second major surface 206 of the sticker 200. The fecal collection receptacle 220 is optionally supplied with a finger tab 230 to facilitate removal of the release layer 228 from the first adhesive 224.

When the wearer defecates, the waste matter passes from the body, through the opening 222 in the anal sticker 200 and directly into the fecal collection receptacle 220, where it remains until the fecal collection receptacle 220 is detached from the anal sticker 200 and discarded.

A female urine collection receptacle, not shown, but similar in appearance and function as the fecal collection receptacle 220, aligns directly with the opening 210' in the female sticker 200' in order to catch the urine. The female urine collection receptacle attaches to the female sticker 200' in the same fashion as the fecal collection receptacle 220 attaches to the anal sticker 200. The female urine collection receptacle contains liquid absorbing material in order to retain the collected urine. The absorbing material can use chemicals or involve chemical processes currently known to those skilled in the art in order to absorb, solidify, or otherwise capture the urine.

When the female wearer urinates, the urine passes from the body, through the opening 210' in the female sticker 200' and directly into the female urine collection receptacle, where it remains until the urine collection receptacle is detached from the female sticker 200' and discarded.

Furthermore, there is the option of adding a plastic lined pocket to the collection receptacles 220, 232 or to the female collection receptacle that was not shown, or to the stickers 200, 200' and 200". The pockets are sized and shaped to be able to house or retain one or more multiple single-use, sanitary, disposable, moist wipes, dry wipes, cleaning wipe, etc therein. When wet wipes are used, they can be sealed inside the pocket in such a fashion that the wet wipes maintain a sanitary and moist condition. The wet wipes are conveniently placed to provide easy access when the user or caregiver needs to remove or replace the stickers or receptacles and clean the skin area. This ensures that cleaning materials are always at hand and also eliminates the need for carrying additional cleaning supplies when away from home.

By separating the liquids from the solids in separate receptacles 220, 232 and the female collection receptacle that was not shown, and keeping all discharges away from the wearer's skin, the incidence of skin irritation and/or skin infection can be minimized, thereby reducing treatment costs for such problems.

Furthermore, the costs involved with producing and implementing this waste collection and containment system are significantly reduced, in comparison to other options. Moreover, the ability to independently change the waste collection receptacles 220 or 232, or the female collection receptacle (not shown), when required, is more economical than replacing a complete diaper. Other cost benefits may be realized as a result of fewer showers, less frequent changing of bedding, and a reduced amount of laundry.

Figure 18:
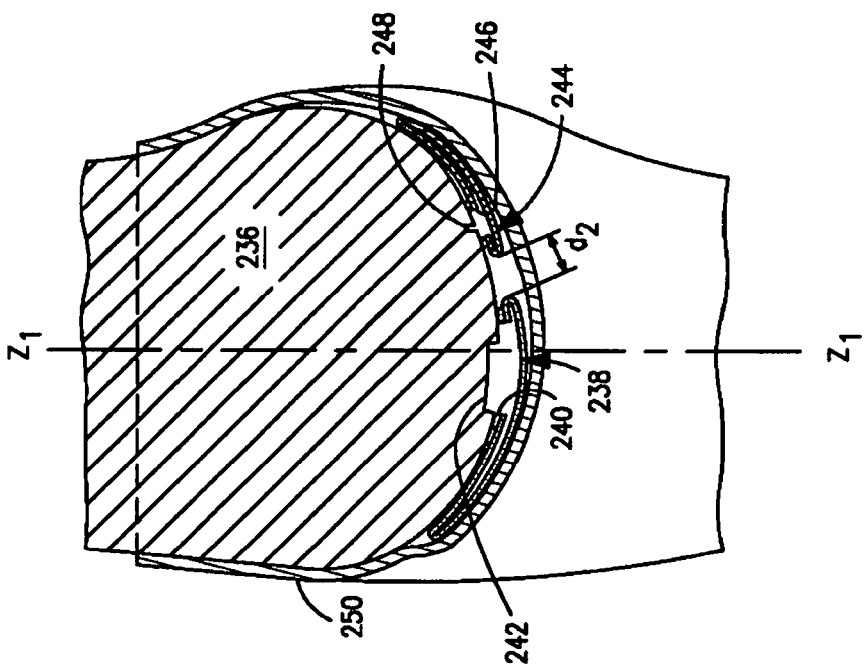
FIG. 18 is a schematic side view of a female human torso sliced vertically in half and showing a disposable urine containment article aligned with a urethral orifice and a disposable fecal containment article aligned with an anal orifice, and the two articles are spaced apart from one another and retained adjacent to the crotch region by an undergarment.

Referring to FIG. 18, a side view of a female human torso 236 is shown sliced vertically in half. A disposable urine containment article 238, having ingress 240, is aligned with a urethral orifice 242 present in the female torso 236. The disposable urine containment article 238 can be positioned adjacent to a user's abdomen. A disposable fecal containment article 244, having ingress 246, is aligned with an anal orifice 248, i.e. the anus. The disposable fecal containment article 244 can be positioned adjacent to a user's buttocks. The disposable urine containment article 238 and the disposable fecal containment article 244 are spaced apart from one another and are retained adjacent to the crotch region of the torso 236 by an undergarment 250. The two disposable containment articles 238 and 244 are separate and distinct articles and the waste collected by one can not be mixed or contacted with the waste collected by the other. The combination of the two disposable containment articles 238 and 244, each capable of collecting body waste from a waste orifice present in a human body, are designed to be simultaneously retained adjacent to the human body by the undergarment 250. The disposable urine containment article can be constructed in a similar fashion as the articles 10, 10' or 11 described above. The ingress 240 is formed in the bodyside layer and is designed to be aligned with the urethral orifice 242 present in the human body. The ingress 240 permits urine to pass from the human body therethrough and be collected in the urine containment article 238.

The disposable fecal containment article 244 can be constructed in a similar fashion as the articles 10 or 10' described above. The ingress 246 is formed in the bodyside layer and is designed to be aligned with the anal orifice 248 present in the human body. The ingress 246 permits fecal matter to pass from the human body therethrough and be collected in the fecal containment article 244.

One will notice that in FIG. 18, the position of the disposable urine containment article 238 is spaced apart from the position of the disposable fecal containment article 244 by a distance $d_2$ when the articles 238 and 244 are initially secured to a human body. In other words, in the embodiment shown in FIG. 18, the disposable urine containment article 238 does not overlap the disposable fecal containment article 244 when the articles 238 and 244 are initially secured to a human body. The distance $d_2$ can vary in dimension and will vary depending on the size of the user, whether a female or a male, and also depending on the position and orientation of the penis in the undergarment 150. Normally, the distance $d_2$ ranges from between about 150 mm to about 5 mm for males and from between about 130 mm to about 5 mm for females. More desirably, the distance $d_2$ ranges from between about 80 mm to about 5 mm. Even more desirably, the distance $d_2$ is at least about 25 mm.

The disposable urine containment article 238 can be removed from the human body and be replaced by another disposable urine containment article 238 while the disposable fecal containment article 244 remains secured to the human body. Likewise, the disposable fecal containment article 244 can be removed from the human body and be replaced by another disposable fecal containment article 244 while the disposable urine containment article 238 remains secured to the human body.

The disposable urine containment article 238 is capable of retaining a predetermined volume of urine and the disposable fecal containment article 244 is capable of retaining an equal or a different volume of fecal matter. Desirably, the disposable urine containment article 238 is capable of retaining from between about 100 ml to about 2,000 ml of urine. More desirably, the disposable urine containment article 238 is capable of retaining from between about 200 ml to about 1,500 ml of urine. Even more desirably, the disposable urine containment article 238 is capable of retaining about 1,000 ml or 1 liter of liquid waste, i.e. urine.

The disposable fecal containment article 244 can have a smaller, a larger or an equal volume capacity as the disposable urine containment article 238. Desirably, the disposable fecal containment article 244 is capable of retaining from between about 100 ml to about 2,000 ml of fecal matter. More desirably, the disposable fecal containment article 244 is capable of retaining from between about 200 ml to about 1,500 ml of fecal matter. Even more desirably, the disposable fecal containment article 244 is capable of retaining about 1,000 ml or 1 liter of semi-solid or solid waste, i.e. fecal matter.

It should be understood that each of the disposable urine containment article 238 and the disposable fecal containment article 244 is capable of receiving multiple insults of body waste. It should also be recognized that the liquid waste, i.e. urine, in the disposable urine containment article 238 is not capable of contacting or mixing with the semi-solid and solid waste, i.e. fecal matter, collected in the disposable fecal containment article 244. Each article 238 and 244 is separate and distinct from the other article.

Figure 19:
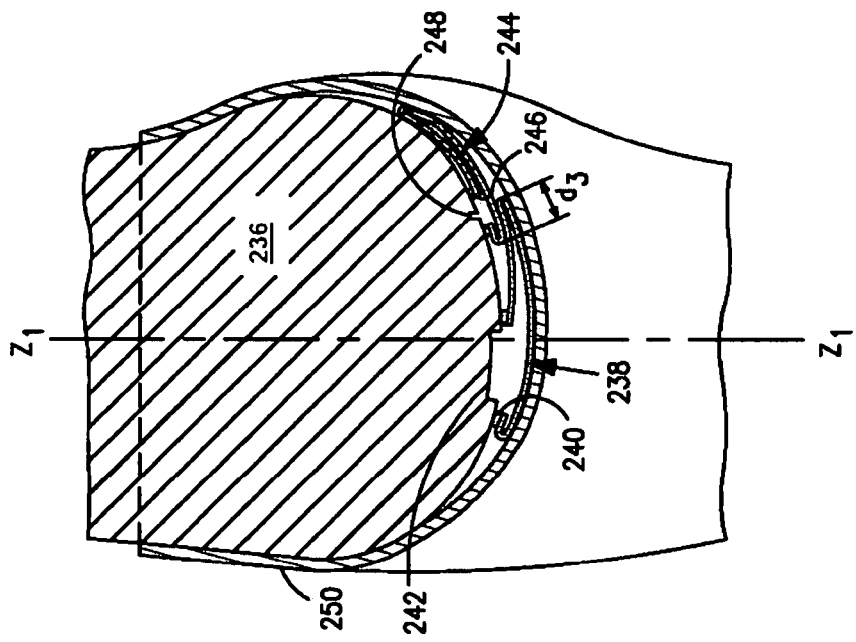
FIG. 19 is a schematic side view of a female human torso sliced vertically in half and showing a disposable urine containment article aligned with a urethral orifice and a disposable fecal containment article aligned with an anal orifice, and at least a portion of the urine containment article overlaps a portion of the fecal containment article and both are retained adjacent to the crotch region by an undergarment.

Referring to FIG. 19, an alternative arrangement is shown for retaining two disposable waste containment articles 238 and 244 adjacent to the crotch region of a human torso 236 by an undergarment 250. In this embodiment, at least a portion of the disposable urine containment article 238, in its initial position, overlaps at least a portion of the disposable fecal containment article 244, when it is in its initial position. The overlap distance $d_3$ can range from between about 2 mm to about 200 mm. Desirably, the overlap distance $d_3$ can range from between about 5 mm to about 150 mm. More desirably, the overlap distance $d_3$ can range from between about 7 mm to about 80 mm. Even more desirably, the overlap distance $d_3$ can range from between about 10 mm to about 50 mm.

It should be understood that another alternative is to arrange the disposable urine containment article 238 and the disposable fecal containment article 244 such that they abut one another in their initial positions. In this embodiment, as in the previous two above described embodiments, each of the disposable waste containment articles 238 and 244 will grow in size, for example, increase in thickness, as they take in body waste discharged from the human torso 236. This enlargement can cause the articles 238 and 244 to move and take on a different orientation within the undergarment 250. Because of this, the location of a partially filled or fully filled article 238 and/or 244 may be different from its initial position.

It should also be recognized that the combination of two disposable waste containment articles, each capable of collecting body waste from a different waste orifice present in a human body, can be affixed or secured to the human body using the stickers 200, 200' and 200" and the receptacles 220 and 232 shown in FIGS. 12-17. Each of the disposable waste containment articles 220 and 232 is designed to be simultaneously retained adjacent to the crotch region of the human body by an undergarment 250. The undergarment 250 desirably contains elastic strands or filaments, or some other type of elastic material that will allow it to stretch and contract during body movement and to accommodate the presence of the two disposable waste containment articles. In this arrangement, a first sticker 200 or 200' is applied to the human body and encompasses a waste orifice, for example a female's urogenital area, as was explained above. A second sticker 200" is applied to the female torso 236 and encompasses her anal orifice. A disposable urine containment article 220 is secured to the first sticker, 200 or 200', and a disposable fecal containment article 232 is secured to the second sticker 200", as was explained above. Each article 220 and 232 will independently collect body waste. The body waste from one orifice is not allowed to mix or contact body waste from the other orifice. When one of the articles 200 or 232 is filled with body waste, it can be removed from its respective sticker 200, 200' or 200" and replaced by a new empty article. Each article 220 and 232 can be changed independent of the other article. As recited above with reference to the articles shown in FIGS. 18 and 19, the two articles 220 and 232 can be spaced apart from one another, abut one another or overlap one another. Each of the two articles 220 and 232 can be manufactured to have a maximum volume and one article 220 or 232 can be sized and configured such that it can accept a smaller, a larger or an equal volume of body waste. Likewise, each article 220 and 232 is capable of receiving multiple insults of body waste. Furthermore, each article 220 and 232 can be constructed such that it is capable of retaining from between about 100 ml to about 2,000 ml of liquid waste, i.e. urine, or semi-solid or solid waste, i.e. fecal matter.

It should be understood that the exact volume that a disposable waste containment article can accept will depend on its size; construction; type of body waste it is taking in; the amount of superabsorbent that is present, if any; the size of the human body it is designed for; the type of body waste it will accept, i.e. liquid, semi-solid, solid; as well as other factors known to those skilled in the art. A disposable waste containment article should have sufficient volume to handle the amount of voided body waste from a particular waste orifice present in a human body. That is, the size of the disposable waste containment article is determined by its end use, whether it is constructed to fit an infant, a toddler, a child or an adult. The size and anatomy of the end user will also dictate the amount of body waste the disposable waste containment article has to handle.

It should further be understood that any of the above described disposable waste containment articles can be symmetrical or asymmetrical in shape.

While the invention has been described in conjunction with several specific embodiments, it is to be understood that many alternatives, modifications and variations will be apparent to those skilled in the art in light of the foregoing description. Accordingly, this invention is intended to embrace all such alternatives, modifications and variations which fall within the spirit and scope of the appended claims.

We claim:

1. A combination of two disposable articles each capable of collecting body waste from a waste orifice present in a human body, each article designed to be simultaneously retained adjacent to the human body by an undergarment, comprising:
   a) a urine containment article having a bodyside, liquid-impermeable layer having a first surface and an outer perimeter, a garment facing, liquid-impermeable layer having an outer perimeter approximately coincident with said outer perimeter of said bodyside layer, an absorbent layer positioned between said bodyside layer and said garment facing layer, a seal bonding at least a portion of said bodyside layer to said garment facing layer, said seal being located inward of said outer perimeters, an ingress formed in said bodyside layer which is designed to be aligned with a urethral orifice present in said human body, said ingress permitting urine to pass from said human body therethrough and be collected in said urine containment article, an adhesive secured to at least a portion of said first surface and at least partially surrounding said ingress, and said urine containment article is capable of retaining from between about 100 ml to about 2,000 ml of urine; and
   b) a fecal containment article having a bodyside, liquid-impermeable layer having a first surface and an outer perimeter, a garment facing, liquid-impermeable layer having an outer perimeter approximately coincident with said outer perimeter of said bodyside layer, an absorbent layer positioned between said bodyside layer and said garment facing layer, a seal bonding at least a portion of said bodyside layer to said garment facing layer, said seal being located inward of said outer perimeters, an ingress formed in said bodyside layer which is designed to be aligned with an anal orifice present in said human body, said ingress permitting fecal matter to pass from said human body therethrough and be collected in said fecal containment article, and an adhesive secured to at least a portion of said first surface and at least partially surrounding said ingress.

2. The combination of claim 1 wherein said urine containment article is positioned adjacent to a user's abdomen and said fecal containment article is positioned adjacent to a user's buttocks.

3. The combination of claim 1 wherein at least a portion of said urine containment article overlaps at least a portion of said fecal containment article when said articles are initially secured to a human body.

4. The combination of claim 1 wherein said urine containment article does not overlap said fecal containment article when said articles are initially secured to a human body.

5. The combination of claim 1 wherein said urine containment article is separated from said fecal containment article by at least about 25 mm when said articles are initially secured to a human body.

6. The combination of claim 1 wherein said urine containment article can be removed from the human body and be replaced by another urine containment article while said fecal containment article remains secured to the human body.

7. The combination of claim 1 wherein said fecal containment article can be removed from the human body and be replaced by another fecal containment article while said urine containment article remains secured to the human body.

8. The combination of claim 1 wherein said urine containment article is capable of retaining a predetermined volume of urine and said fecal containment article is capable of retaining a different volume of fecal matter.

9. The combination of claim 1 wherein said urine containment article is capable of retaining a predetermined volume of urine and said fecal containment article is capable of retaining an equal volume of fecal matter.

10. The combination of claim 1 wherein said urine containment article is capable of retaining from between about 200 ml to about 1,500 ml of urine.

11. The combination of claim 1 wherein said fecal containment article is capable of retaining from between about 100 ml to about 2,000 ml of fecal matter.

12. The combination of claim 1 wherein each of said urine containment article and said fecal containment article is capable of receiving multiple insults of body waste.

13. The combination of claim 1 wherein urine collected by said urine containment article does not mix with fecal matter collected by said fecal containment article.

14. A combination of two disposable articles each capable of collecting body waste from a waste orifice present in a human body, each article designed to be simultaneously retained adjacent to the human body by an undergarment, comprising:
   a) a first sticker having a first member with a first major surface, a second major surface, and a body adhesive secured to said first major surface, said first sticker having an aperture formed therethrough, an inner periphery and an outer periphery, said body adhesive allowing said first sticker to be removably attached to a human body such that said inner periphery surrounds a urethral orifice;
   b) a urine containment article having a bodyside, liquid-impermeable layer having a first surface and an outer perimeter, a garment facing, liquid-impermeable layer having an outer perimeter approximately coincident with said outer perimeter of said bodyside layer, an absorbent layer positioned between said bodyside layer and said garment facing layer, a seal bonding at least a portion of said bodyside layer to said garment facing layer, said seal being located inward of said outer perimeters, an ingress formed in said bodyside layer which is designed to be aligned with a urethral orifice present in said human body, said ingress permitting urine to pass from said human body therethrough and be collected in said urine containment article, and an adhesive secured to at least a portion of said first surface and at least partially surrounding said ingress, said adhesive removably securing said urine containment article to said second major surface of said first sticker;
   c) a second sticker having a first member with a first major surface, a second major surface, and a body adhesive secured to said first major surface, said second sticker having an aperture formed therethrough, an inner periphery and an outer periphery, said body adhesive allowing said second sticker to be removably attached to a human body such that said inner periphery surrounds an anal orifice; and
   d) a fecal containment article having a bodyside, liquid-impermeable layer having a first surface and an outer perimeter, a garment facing, liquid-impermeable layer having an outer perimeter approximately coincident with said outer perimeter of said bodyside layer, an absorbent layer positioned between said bodyside layer and said garment facing layer, a seal bonding at least a portion of said bodyside layer to said garment facing layer, said seal being located inward of said outer perimeters, an ingress formed in said bodyside layer which is designed to be aligned with an anal orifice present in said human body, said ingress permitting fecal matter to pass from said human body therethrough and be collected in said fecal containment article, an adhesive secured to at least a portion of said first surface and at least partially surrounding said ingress, said adhesive removably securing said urine containment article to said second major surface of said second sticker, and said fecal containment article is capable of retaining from between about 100 ml to about 2,000 ml of fecal matter.

15. The combination of claim 14 wherein said urine containment article and said fecal containment article are removably secured to said first and second stickers, respectively, by an adhesive.

16. The combination of claim 14 wherein said urine containment article is capable of retaining a predetermined volume of urine and said fecal containment article is capable of retaining a different volume of fecal matter.

17. The combination of claim 14 wherein said urine containment article is capable of retaining from between about 100 ml to about 2,000 ml of urine.

18. The combination of claim 14 wherein said fecal containment article is capable of retaining from between about 200 ml to about 1,500 ml of fecal matter.

19. The combination of claim 14 wherein said urine containment article overlaps at least a portion of said fecal containment article when both are simultaneously retained adjacent to the human body by said undergarment.

20. A combination of two disposable articles each capable of collecting body waste from a waste orifice present in a human body, each article designed to be simultaneously worn on the human body, comprising:
   a) a urine containment article having a liquid-impermeable bodyside layer having a body facing first surface and an outer perimeter, a liquid-impermeable garment facing layer having an outer perimeter approximately coincident with said outer perimeter of said bodyside layer, an absorbent layer positioned between said bodyside layer and said garment facing layer, an acquisition layer positioned between said bodyside layer and said absorbent layer, said acquisition layer having an outer perimeter approximately coincident with said outer perimeter of said bodyside layer, and said acquisition layer capable of distributing body waste across said absorbent layer, a seal bonding at least a portion of said bodyside layer, said acquisition layer and said garment facing layer together, said seal being located inward of said outer perimeters, an ingress formed in said bodyside layer which is designed to be aligned with a urethral orifice present in said human body, said ingress permitting urine to pass from said human body therethrough and be collected in said urine containment article, and an adhesive secured to at least a portion of said body facing first surface and at least partially surrounding said ingress; and
   b) a fecal containment article having a liquid-impermeable bodyside layer having a body facing first surface and an outer perimeter, a liquid-impermeable garment facing layer having an outer perimeter approximately coincident with said outer perimeter of said bodyside layer, an absorbent layer positioned between said bodyside layer and said garment facing layer, a seal bonding at least a portion of said bodyside layer, said absorbent layer and said garment facing layer together, said seal being located inward of said outer perimeters, an ingress formed in said bodyside layer which is designed to be aligned with an anal orifice present in said human body, said ingress permitting fecal matter to pass from said human body therethrough and be collected in said fecal containment article, an adhesive secured to at least a portion of said body facing first surface of said fecal containment article and at least partially surrounding said ingress, and an acquisition layer positioned between said bodyside layer and said absorbent layer, said acquisition layer having an outer perimeter approximately coincident with said outer perimeter of said bodyside layer, and said acquisition layer capable of distributing body waste across said absorbent layer.

21. The combination of claim 1 wherein said fecal containment article includes an acquisition layer positioned between said bodyside layer and said absorbent layer, said acquisition layer having an outer perimeter approximately coincident with said outer perimeter of said bodyside layer, and said acquisition layer capable of distributing body waste across said absorbent layer.

22. The combination of claim 14 wherein said fecal containment article includes an acquisition layer positioned between said bodyside layer and said absorbent layer, said acquisition layer having an outer perimeter approximately coincident with said outer perimeter of said bodyside layer, and said acquisition layer capable of distributing body waste across said absorbent layer.

* * * * *